US012653785B2

(12) United States Patent
Acharya et al.

(10) Patent No.: US 12,653,785 B2
(45) **Date of Patent: *Jun. 16, 2026**

(54) COMPOSITIONS AND METHODS FOR ADMINISTERING A YAP1/WWRT1 INHIBITING COMPOSITION AND A GLS1 INHIBITING COMPOSITION

(71) Applicant: UNIVERSITY OF PITTSBURGH—OF THE COMMONWEALTH SYSTEM OF HIGHER EDUCATION, Pittsburgh, PA (US)

(72) Inventors: Abhinav Prakash Acharya, Pittsburgh, PA (US); Stephen Yu-Wah Chan, Pittsburgh, PA (US); Steven R. Little, Allison Park, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/350,304

(22) Filed: Jul. 11, 2023

(65) Prior Publication Data

US 2024/0082158 A1 Mar. 14, 2024

Related U.S. Application Data

(63) Continuation of application No. 16/765,977, filed on May 21, 2020, now abandoned.

(51) Int. Cl.

*A61K 9/16* (2006.01)
*A61K 31/409* (2006.01)

(Continued)

(52) U.S. Cl.

CPC .......... *A61K 9/1647* (2013.01); *A61K 31/409* (2013.01); *A61K 31/4545* (2013.01); *A61K 31/473* (2013.01); *A61K 31/501* (2013.01)

(58) Field of Classification Search

None

See application file for complete search history.

(56) References Cited

U.S. PATENT DOCUMENTS 4,938,949 A 7/1990 Borch et al.
5,707,608 A 1/1998 Liu (Continued)

FOREIGN PATENT DOCUMENTS

CA 2956256 A1 2/2016
EP 3713569 B1 3/2024

(Continued)

OTHER PUBLICATIONS

Klose et al. "How porosity and size effect the drug release mechanisms from PLGA-based microparticles", International Journal of Pharmaceutics, vol. 314, Issue 2, May 18, 2006, pp. 198-206. (Year: 2006).*

(Continued)

*Primary Examiner* — Carlos A Azpuru
*Assistant Examiner* — Casey S Hagopian
(74) *Attorney, Agent, or Firm* — Meunier Carlin & Curfman LLC

(57) ABSTRACT

Disclosed are compositions comprising a YAP1/WWRT1 inhibiting agent and a glutaminase inhibiting agent and methods of their use. Disclosed herein are therapeutic particles comprising a biocompatible polymer, a YAP1/WWRT1 inhibiting agent, and a glutaminase inhibiting agent. In one aspect, disclosed herein are methods of treating (Continued)

Figure 1:
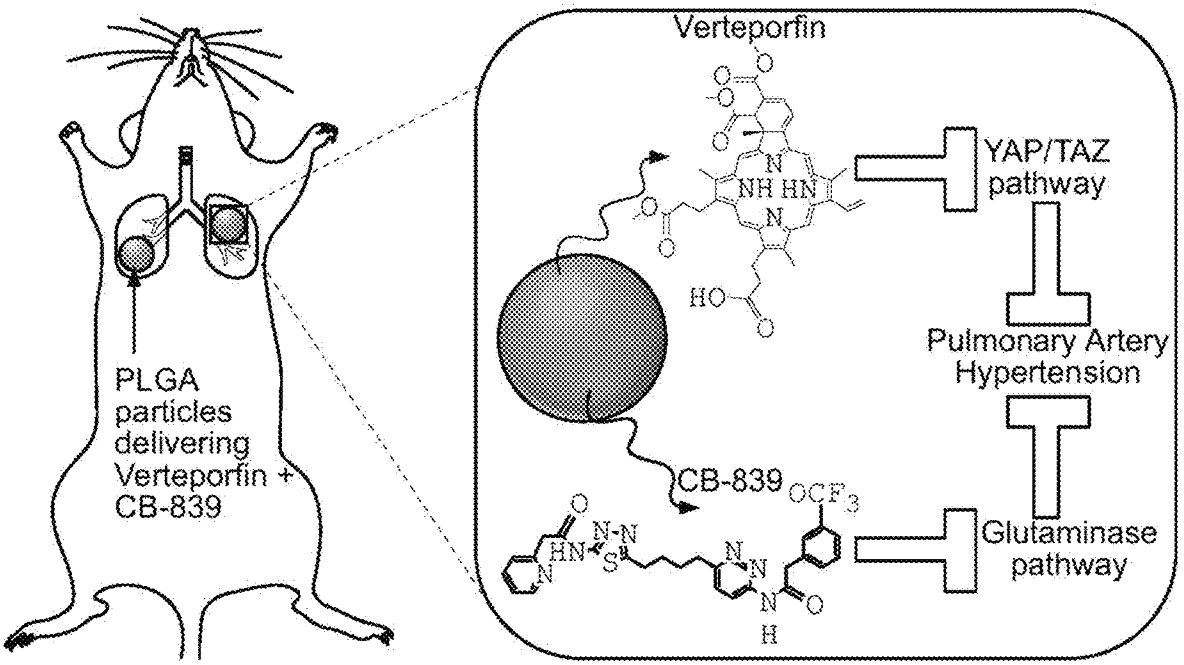

a pulmonary disease in a subject in need of such treatment comprising administering the therapeutic particle to the subject.

8 Claims, 7 Drawing Sheets

Specification includes a Sequence Listing.

(51) Int. Cl.

| | |
|---|---|
| *A61K 31/4545* | (2006.01) |
| *A61K 31/473* | (2006.01) |
| *A61K 31/501* | (2006.01) |

(56) References Cited

U.S. PATENT DOCUMENTS

| | | | | |
|---|---|---|---|---|
| 5,756,541 | A | 5/1998 | Strong et al. | |
| 5,798,345 | A | 8/1998 | Knutson et al. | |
| 8,466,283 | B2 | 6/2013 | Hentemann | |
| 8,604,016 | B2 | 12/2013 | Li et al. | |
| 8,865,718 | B2 | 10/2014 | Li et al. | |
| 10,925,869 | B2 * | 2/2021 | Chan | A61P 9/00 |
| 11,672,795 | B2 * | 6/2023 | Chan | A61P 9/00 514/284 |
| 2005/0119330 | A1 | 6/2005 | Kao et al. | |
| 2005/0244504 | A1 | 11/2005 | Little et al. | |
| 2009/0202540 | A1 | 8/2009 | Gant | |
| 2009/0317478 | A1 | 12/2009 | Han et al. | |
| 2011/0091421 | A1 | 4/2011 | Mann | |
| 2013/0259923 | A1 | 10/2013 | Bancel et al. | |
| 2015/0258082 | A1 | 9/2015 | Parlati et al. | |
| 2016/0058759 | A1 | 3/2016 | Heffernan et al. | |
| 2016/0287585 | A1 * | 10/2016 | Parlati | A61K 31/501 |
| 2017/0209387 | A1 * | 7/2017 | Hanes | A61P 35/00 |
| 2017/0290815 | A1 | 10/2017 | Mcdermott et al. | |
| 2020/0276125 | A1 | 9/2020 | Acharya et al. | |

FOREIGN PATENT DOCUMENTS

| | | | |
|---|---|---|---|
| JP | 2022119825 | A | 8/2022 |
| WO | 2015171641 | | 11/2015 |
| WO | 2016007647 | A1 | 1/2016 |
| WO | 2016054388 | | 4/2016 |
| WO | 2016/077632 | | 5/2016 |
| WO | 2016130889 | | 8/2016 |
| WO | 2017004310 | | 1/2017 |
| WO | 2017/095751 | | 6/2017 |
| WO | 2017/205595 | | 11/2017 |
| WO | 2019104038 | A1 | 5/2019 |

OTHER PUBLICATIONS

Bertero et al. "Vascular stiffness mechanoactivates YAP/TAZ-dependent glutaminolysis to drive pulmonary hypertension", The Journal of Clinical Investigation, Sep. 2016, vol. 126, No. 9, pp. 3313-3335. (Year: 2016).*

Mcdermott Lee A. et al., "Design and Evaluation of Novel Glutaminase Inhibitors", Bioorganic and Medicinal Chemistry, vol. 24, No. 8, Apr. 1, 2016 (Apr. 1, 2016), pp. 1819-1839, XP055844153, Amsterdam, NL ISSN: 0968-0896, DOI 10.1016/j.bmc.2016.03.009.

Liu, Bin et al., "Oxidative stress and pulmonary arterial hypertension vascular modeling", Chinese Journal of Arteriosclerosis, 06, pp. 539-542.

Bertero et al., "Matrix remodeling promotes pulmonary hypertension through feedback mechanoactivation of the YAP/TAZ-miR-130/301 circuit", Cell Rep. Issue 13, No. 5, pp. 1016-1032.

Acharya AP, Carstens MR, Lewis JS, Dolgova N, Xia CQ, Clare-Salzler MJ and Keselowsky BG. A cell-based microarray to investigate combinatorial effects of microparticle-encapsulated adjuvants on dendritic cell activation. J Mater Chem B. 2016;4:1672-1685.

Acharya AP, Clare-Salzler MJ and Keselowsky BG. A high-throughput microparticle microarray platform for dendritic cell-targeting vaccines. Biomaterials. 2009;30:4168-77.

Acharya et al., "Simultaneous Pharmacologic Inhibition of Yes-Associated Protein 1 and Glutaminase 1 via Inhaled Poly(Lactic-co-Glycolic) Acid-Encapsulated Microparticles Improves Pulmonary Hypertension", 2021, J. Am. Heart Assoc., 10(12), pp. 1-15. (DOI: 10.1161/JAHA.120.019091) (Year: 2021).

Arnold JJ. Age-related macular degeneration: anti-vascular endothelial growth factor treatment. BMJ Clin Evid. 2016, 0701.

Bagshawe, K. D. Towards generating cytotoxic agents at cancer sites. The First Bagshawe Lecture. Br. J. Cancer 60 (1989): 275-281.

Bagshawe, K. D., et al. A cytotoxic agent can be generated selectively at cancer sites. British journal of cancer 58.6 (1988): 700-703.

Battelli, M. G., et al. T lymphocyte killing by a xanthine-oxidase-containing immunotoxin. Cancer Immunology, Immunotherapy 35.6 (1992): 421-425.

Bertero et al. "Vascular Stiffness Mechanoactivates YAP/TAZ-Dependent Glutaminolysis to Drive Pulmonary Hypertension", Journal of Clinical Investigation, Sep. 1, 2016, vol. 126, Iss. 9, pp. 3313-3335.

Bertero T, Cotrill KA, Lu Y, Haeger CM, Dieffenbach P, Annis S, Hale A, Bhat B, Kaimal V, Zhang YY, Graham BB, Kumar R, Saggar R, Saggar R, Wallace WD, Ross DJ, Black SM, Fratz S, Fineman JR, Vargas SO, Haley KJ, Waxman AB, Chau BN, Fredenburgh LE and Chan SY. Matrix remodeling promotes pulmonary hypertension through feedback mechanoactivation of the YAP/TAZ-miR-130/301 circuit Cell Reports. 2015;13:1016-1032.

Bertero T, Lu Y, Annis S, Hale A, Bhat B, Saggar R, Saggar R, Wallace WD, Ross DJ, Vargas SO, Graham BB, Kumar R, Black SM, Fratz S, Fineman JR, West JD, Haley KJ, Waxman AB, Chau BN, Cottrill KA and Chan SY. Systems-level regulation of microRNA networks by miR-130/301 promotes pulmonary hypertension. J Clin Invest. 2014;124:3514-28.

Birsoy K, et al., An essential role of the mitochondrial electron transport chain in cell proliferation is to enable aspartate synthesis, Cell. 2015;162(3):540-51.

Brown, Valerie I., and Mark I. Greene. Molecular and cellular mechanisms of receptor-mediated endocytosis. DNA and cell biology 10.6 (1991): 399-409.

Chan SY and Loscalzo J. Pathogenic mechanisms of pulmonary arterial hypertension. J Mol Cell Cardiol. 2008;44:14-30.

Chan SY and Rubin LJ. Metabolic dysfunction in pulmonary hypertension: From basic science to clinical practice European Respiratory Review: An Official Journal of the European Respiratory Society. 2017;26:pii: 170094.

Chatterjee, Dev Kumar, Li Shan Fong, and Yong Zhang. "Nanoparticles in photodynamic therapy: an emerging paradigm." Advanced drug delivery reviews 60.15 (2008): 1627-1637.

Chen, L., et al., "Targeting Glutamine Induces Apoptosis: A Cancer Therapy Approach," International Journal of Molecular Sciences, vol. 16, 2015, pp. 22830-22855.

Communication Pursuant to Rule 164(1) EPC dated Mar. 12, 2020, issued in Application No. EP17803564.8, 10 pages.

Cottrill KA, et al., Metabolic dysfunction in pulmonary hypertension: the expanding relevance of the Warburg effect. European J. of Clin. Invest. 2013;43(8):855-65.

Cowan K, et al., Complete reversal of fatal pulmonary hypertension in rats by a serine elastase inhibitor, Nature Medicine. 2000;6(6):698-702.

De Vitto, Humberto, Juan Perez-Valencia, and James A. Radosevich. "Glutamine at focus: versatile roles in cancer." Tumor Biology 37.2 (2016): 1541-1558.

Decision to Grant, dated Apr. 19, 2022, received in connection with related JP Patent Application No. 2018-561938 (translation), 2 pages.

Decision to Grant, dated May 17, 2022, received in conneciton with related KR Patent Application No. 10-2018-7037697 (translation), 6 pages.

Deng, Wei, et al. "PLGA nanocomposites loaded with verteporfin and gold nanoparticles for enhanced photodynamic therapy of cancer cells." RSC advances 6.113 (2016): 112393-112402.

(56) References Cited

OTHER PUBLICATIONS

Diebold I, et al., BMPR2 preserves mitochondrial function and DNA during reoxygenation to promote endothelial cell survival and reverse pulmonary hypertension, Cell Metabolism. 2015;21(4):596-608.
Dieffenbach PB, Haeger CM, Coronata AMF, Choi KM, Varelas X, Tschumperlin DJ and Fredenburgh LE. Arterial stiffness induces remodeling phenotypes in pulmonary artery smooth muscle cells via YAP/TAZ-mediated repression of cyclooxygenase-2. Am J Physiol Lung Cell Mol Physiol. 2017;313:L628-L647.
Dumas SJ, Bru-Mercier G, Courboulin A, Quatredeniers M, Rucker-Martin C, Antigny F, Nakhleh MK, Ranchoux B, Gouadon E, Vinhas MC, Vocelle M, Raymond N, Dorfmuller P, Fadel E, Perros F, Humbert M and Cohen-Kaminsky S. NMDA-Type Glutamate Receptor Activation Promotes Vascular Remodeling and Pulmonary Arterial Hypertension. Circulation. 2018.
Dumas, et al., "[The paradigm of cancer in pulmonary arterial hypertension: towards anti-remodeling therapies targeting metabolic dysfunction?]" Biol Aujourdhui. 2016;210(4):171-189. See Machine Translation. English Abstract.
Dupont S, Morsut L, Aragona M, Enzo E, Giulitti S, Cordenonsi M, Zanconato F, Le Digabel J, Forcato M, Bicciato S, Elvassore N and Piccolo S. Role of YAP/TAZ in mechanotransduction. Nature. 2011;474:179-83.
Elgogary, Amira, et al. "Combination therapy with BPTES nanoparticles and metformin targets the metabolic heterogeneity of pancreatic cancer." Proceedings of the National Academy of Sciences 113.36 (2016): E5328-E5336.
Enzo E, et al., Aerobic glycolysis tunes YAP/TAZ transcriptional activity. EMBO J. 2015;34(10):1349-70.
Examination report No. 1 issued for Australian Application No. 2017270092, dated Mar. 1, 2022.
Extended EP Search Report dated Jun. 25, 2020, from related EP Application No. 17803564.8, 10 pages.
Extended European Search report issued for Application No. 18881514.6, dated Jul. 16, 2021.
Extended European Search report issued for Application No. 21205602.2, dated Feb. 18, 2022.
Ferrone et al., eds., Noges Publications, Park Ridge, N.J., (1985) ch. 22 and pp. 303-357.
Fisher JD, Acharya AP and Little SR. Micro and nanoparticle drug delivery systems for preventing allotransplant rejection. Clin Immunol. 2015; 160:24-35.
Freireich et al., Quantitative comparison of toxicity of anticancer agents in mouse, rat, hamster, dog, monkey, and man. Cancer Chemother Reports, 1966, 50(4):219-244.
Ge J, Cui H, Xie N, Banerjee S, Guo S, Dubey S, Barnes S and Liu G. Glutaminolysis Promotes Collagen Translation and Stability via alpha-Ketoglutarate-mediated mTOR Activation and Proline Hydroxylation. Am J Respir Cell Mol Biol. 2018;58:378-390.
Godinas L, Guignabert C, Seferian A, Perros F, Bergot E, Sibille Y, Humbert M and Montani D. Tyrosine kinase inhibitors in pulmonary arterial hypertension: a double-edge sword? Semin Respir Crit Care Med. 2013;34:714-24.
Hoeper MM, Barst RJ, Bourge RC, Feldman J, Frost AE, Galie N, Gomez-Sanchez MA, Grimminger F, Grunig E, Hassoun PM, Morrell NW, Peacock AJ, Satoh T, Simonneau G, Tapson VF, Torres F, Lawrence D, Quinn DA and Ghofrani HA. Imatinib mesylate as add-on therapy for pulmonary arterial hypertension: results of the randomized IMPRES study. Circulation. 2013;127:1128-38.
Hu J, Xu Q, McTiernan C, Lai YC, Osei-Hwedieh D and Gladwin M. Novel Targets of Drug Treatment for Pulmonary Hypertension. Am J Cardiovasc Drugs. 2015;15:225-34.
Hughes, Brenda J., et al. Monoclonal antibody targeting of liposomes to mouse lung in vivo. Cancer research 49.22 (1989): 6214-6220.
Humbert M, Sitbon O and Simonneau G. Treatment of pulmonary arterial hypertension. N Engl J Med. 2004;351:1425-36.
International Preliminary Report on Patentability issued for Application No. PCT/US2018/062013, dated Jun. 4, 2020.
International Search Report and Written Opinion dated Feb. 14, 2019, from International Application No. PCT/US2018/062013, 11 pages.
International Search Report and Written Opinion issued for International Application No. PCT/US2017/034420, dated Aug. 16, 2017.
Jain RA. The manufacturing techniques of various drug loaded biodegradable poly(lactide-co-glycolide) (PLGA) devices. Biomaterials. 2000;21:2475-90.
Katt, William P., et al. "Dibenzophenanthridines as Inhibitors of Glutaminase C and Cancer Cell ProliferationCharacterization of a New Class of Glutaminase Inhibitors." Molecular cancer therapeutics 11.6 (2012): 1269-1278.
Kimura et al. The Hippo pathway mediates inhibition of vascular smooth muscle cell proliferation by cAMP. Journal of Molecular and Cellular Cardiology, Nov. 25, 2015 (Nov. 25, 2015), vol. 90, pp. 1-10.
Kudryashova TV, Goncharov DA, Pena A, Kelly N, Vanderpool R, Baust J, Kobir A, Shufesky W, Mora AL, Morelli AE, Zhao J, Ihida-Stansbury K, Chang B, DeLisser H, Tuder RM, Kawut SM, Sillje HH, Shapiro S, Zhao Y and Goncharova EA. HIPPO-Integrin-linked Kinase Cross-Talk Controls Self-Sustaining Proliferation and Survival in Pulmonary Hypertension. Am J Respir Crit Care Med. 2016;194:866-877.
Lammers S, et al., Mechanics and function of the pulmonary vasculature: implications for pulmonary vascular disease and right ventricular function. Compr Physiol. 2012;2(1):295-319.
Le A, et al., Glucose-independent glutamine metabolism via TCA cycling for proliferation and survival in B cells. Cell metabolism. 2012; 15(1):110-21.
Litzinger and Huang, Biochimica et Biophysica Acta, 1104:179-187, (1992).
Liu, Lagares D, Choi KM, Stopfer L, Marinkovic A, Vrbanac V, Probst CK, Hiemer SE, Sisson TH, Horowitz JC, Rosas IO, Fredenburgh LE, Feghali-Bostwick C, Varelas X, Tager AM and Tschumperlin DJ. Mechanosignaling through YAP and TAZ drives fibroblast activation and fibrosis. Am J Physiol Lung Cell Mol Physiol. 2015;308:L344-57.
Lo Sardo F, Strano S and Blandino G. YAP and TAZ in Lung Cancer: Oncogenic Role and Clinical Targeting. Cancers (Basel). 2018; 10.
Lunt SY, et al., Aerobic glycolysis: meeting the metabolic requirements of cell proliferation. Annu Rev Cell Dev Biol. 2011;2:441-64.
Mathiowitz and Langer, Polyanhydride microspheres as drug carriers I. Hot-melt microencapsulation. J Controlled Release, 1987, 5:13-22.
Mathiowitz et al., Novel microcapsules for delivery systems. Reactive Polymers, 1987, 6:275-283.
Mathiowitz et al., Polyanhydride microspheres as drug carriers. II. Microencapsulation by solvent removal. J. Appl. Polymer Sci, 1988, 35:755-774.
Mecham RP, et al., "Smooth muscle-mediated connective tissue remodeling in pulmonary hypertension", Science. 1987;237(4813):423-6.
Michelakis ED, Gurtu V, Webster L, Barnes G, Watson G, Howard L, Cupitt J, Paterson I, Thompson RB, Chow K, O'Regan DP, Zhao L, Wharton J, Kiely DG, Kinnaird A, Boukouris AE, White C, Nagendran J, Freed DH, Wort SJ, Gibbs JSR and Wilkins MR. Inhibition of pyruvate dehydrogenase kinase improves pulmonary arterial hypertension in genetically susceptible patients. Sci Transl Med. 2017;9.
Mo JS, et al., Cellular energy stress induces AMPK-mediated regulation of YAP and the Hippo pathway. Nat Cell Biol. 2015;17(4):500-10.
Nave AH, et al., Lysyl oxidases play a causal role in vascular remodeling in clinical and experimental pulmonary arterial hypertension. Arteriosclerosis, thrombosis, and vascular biology. 2014; 34(7):1446-58.
Non-Final Office Action issued for U.S. Appl. No. 16/303,369, dated Feb. 21, 2020.
Notice of Allowance issued for U.S. Appl. No. 16/303,369, dated Jun. 18, 2020.

(56)                    References Cited

OTHER PUBLICATIONS

Notice of Allowance issued for U.S. Appl. No. 17/148,701, dated Feb. 3, 2023.

Office Action dated Jun. 15, 2021, received in related JP Application No. 2018-561938, 10 pages.

Office Action issued for Japanese Application No. 2020528156, dated Nov. 22, 2022.

Office Action issued in U.S. Appl. No. 17/148,701 dated Sep. 7, 2022.

Pan D., The Hippo Signaling Pathway in Development and Cancer. Dev Cell. 2010;19(4):491-505.

Paulin R, et al., The metabolic theory of pulmonary arterial hypertension. Circ. Res. 2014;115(1):148-64.

Piao L, et al., Cardiac glutaminolysis: a maladaptive cancer metabolism pathway in the right ventricle in pulmonary hypertension. Journal of molecular medicine. 2013;91(10):1185-97.

Piersma, B., Bank, R. A., & Boersema, M. (2015). Signaling in Fibrosis: TGF-β, WNT, and YAP/TAZ Converge. Frontiers in Medicine, 2. doi: 10.3389/fmed.2015.00059.

Piersma, Bram, Ruud A. Bank, and Miriam Boersema. Signaling in fibrosis: TGF-β, WNT, and YAP/TAZ converge. Frontiers in medicine 2 (2015): 59.

Pietersz, Geoffrey A., and Ian FC McKenzie. Antibody conjugates for the treatment of cancer. Immunological reviews 129.1 (1992): 57-80.

Pullamsetti SS, Savai R, Seeger W and Goncharova EA. Translational Advances in the Field of Pulmonary Hypertension. From Cancer Biology to New Pulmonary Arterial Hypertension Therapeutics. Targeting Cell Growth and Proliferation Signaling Hubs. Am J Respir Crit Care Med. 2017;195:425-437.

Ratay ML, Balmert SC, Acharya AP, Greene AC, Meyyappan T and Little SR. TRI Microspheres prevent key signs of dry eye disease in a murine, inflammatory model. Sci Rep. 2017;7: 17527.

Roffler, Steven R., et al. Anti-neoplastic glucuronide prodrug treatment of human tumor cells targeted with a monoclonal antibody-enzyme conjugate. Biochemical pharmacology 42.10 (1991): 2062-2065.

Romero R, Sayin VI, Davidson SM, Bauer MR, Singh SX, LeBoeuf SE, Karakousi TR, Ellis DC, Bhutkar A, Sanchez-Rivera FJ, Subbaraj L, Martinez B, Bronson RT, Prigge JR, Schmidt EE, Thomas CJ, Goparaju C, Davies A, Dolgalev I, Heguy A, Allaj V, Poirier JT, Moreira AL, Rudin CM, Pass HI, Vander Heiden MG, Jacks T and Papagiannakopoulos T. Keap1 loss promotes Kras-driven lung cancer and results in dependence on glutaminolysis. Nat Med. 2017;23:1362-1368.

Schneider CS, Xu Q, Boylan NJ, Chisholm J, Tang BC, Schuster BS, Henning A, Ensign LM, Lee E, Adstamongkonkul P, Simons BW, Wang SS, Gong X, Yu T, Boyle MP, Suk JS and Hanes J.

Nanoparticles that do not adhere to mucus provide uniform and long-lasting drug delivery to airways following inhalation. Sci Adv. 2017;3:e1601556.

Senter, Peter D., et al. Generation of 5-fluorouracil from 5-fluorocytosine by monoclonal antibody-cytosine deaminase conjugates. Bioconjugate chemistry 2.6 (1991): 447-451.

Senter, Peter D., et al. Generation of cytotoxic agents by targeted enzymes. Bioconjugate chemistry 4.1 (1993): 3-9.

Smith et al., Antibodies in Human Diagnosis and Therapy, Haber et al., eds., Raven Press, New York (1977) pp. 365-389.

Sullivan LB, et al., Supporting aspartate biosynthesis is an essential function of respiration in proliferating cells. Cell. 2015;162(3):552-63.

Tian, Lian, and Naomi C. Chester. "In vivo and in vitro measurements of pulmonary arterial stiffness: a brief review." Pulmonary circulation 2.4 (2012): 505-517.

Van Den Heuvel, A. Pieter J., et al. "Analysis of glutamine dependency in non-small cell lung cancer: GLS1 splice variant GAC is essential for cancer cell growth." Cancer biology & therapy 13.12 (2012): 1185-1194.

Wang W, et al., AMPK modulates Hippo pathway activity to regulate energy homeostasis. Nat Cell Biol. 2015;17(4):490-9.

Wang, C. et al. "Verteporfin inhibits YAP function through up-regulating 14-3-3o sequestering YAP in the cytoplasm", Am J Cancer Res, Jan. 1, 2016, 6(1), 27-37.

Zamanian RT, Levine DJ, Bourge RC, De Souza SA, Rosenzweig EB, Alnuaimat H, Burger C, Mathai SC, Leedom N, DeAngelis K, Lim A and De Marco T. An observational study of inhaled-treprostinil respiratory-related safety in patients with pulmonary arterial hypertension. Pulm Circ. 2016;6:329-37.

Zhao L, et al. The zinc transporter ZIP12 regulates the pulmonary vascular response to chronic hypoxia. Nature. 2015;524(7565):356-60.

Zhao Y, et al., Targeting cellular metabolism to improve cancer therapeutics. Cell Death Dis. 2013;4(e532).

Office Action received in connection with Japanese Application No. 2022-079875, dated Jun. 6, 2023, 8 pages.

Office Action received in connection with Canadian Application No. 3,025,401, dated Jul. 7, 2023, 5 pages.

Chinese Journal of Arteriosclerosis, Jun. 26, 2011, Bin Liu; Jun Peng; Oxidative Stress and pulmonary arterial hypertension vascular remodeling, pp. 539-542.

Rytting, E.; et al., "Biodegradable polymeric nanocarriers for pulmonary drug delivery", Expert Opin. Drug Deliv., 5/6, pp. 629-639, DOI: https://doi.org/10.1517/17425247.5.6.629, Jun. 5, 2008 (Jun. 5, 2008).

Canadian Intellectual Property Office. Office Action issued in Canadian Application No. 3082148. Nov. 29, 2023. 7 pages.

Examination Report issued in corresponding Canadian Application No. 3,082, 148, issued on Nov. 5, 2024, 4 pages.

* cited by examiner

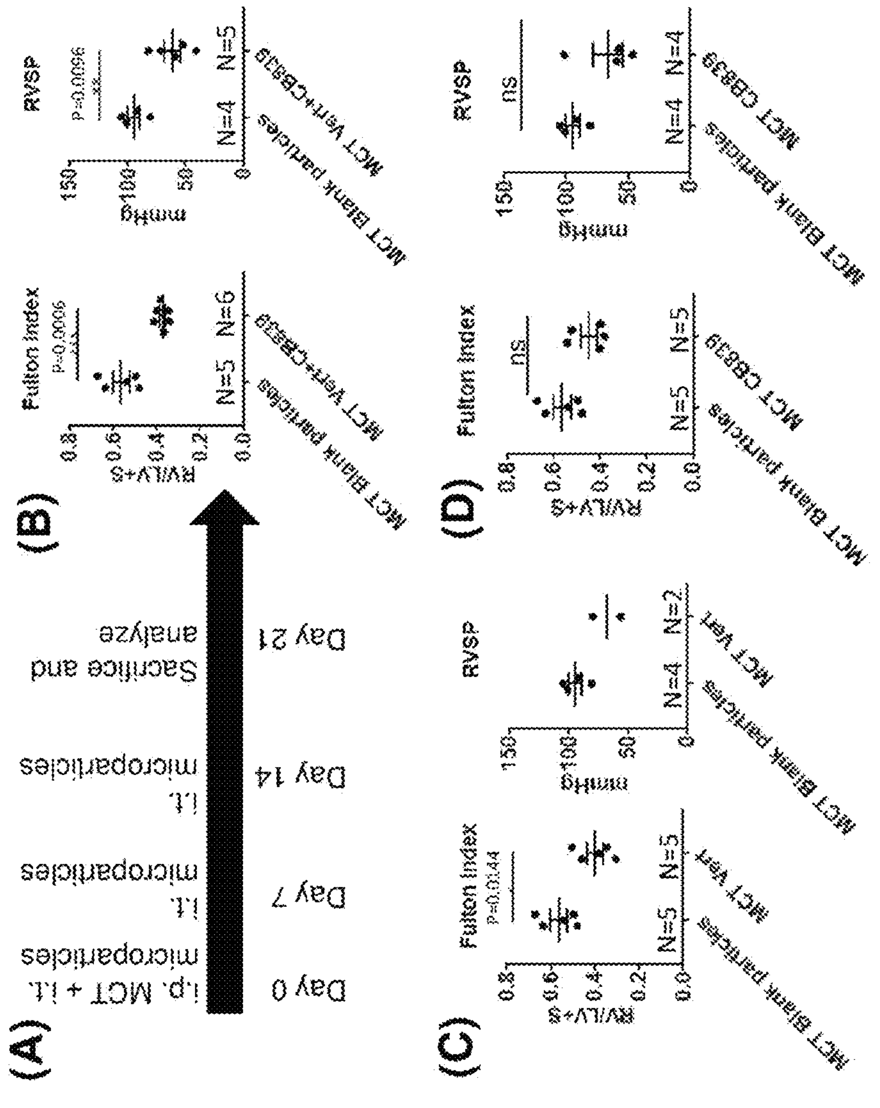
FIG. 4A, FIG. 4B, FIG. 4C, and FIG. 4D

SEQUENCE LISTING

```
Sequence total quantity: 6
SEQ ID NO: 1           moltype = AA  length = 400
FEATURE                Location/Qualifiers
source                 1..400
                       mol_type = protein
                       organism = Homo sapiens
SEQUENCE: 1
MNPASAPPPL PPPGQQVIHV TQDLDTDLEA LFNSVMNPKP SSWRKKILPE SFFKEPDSGS  60
HSRQSSTDSS GGHPGPRLAG GAQHVRSHSS PASLQLGTGA GAAGSPAQQH AHLRQQSYDV  120
TDELPLPPGW EMTFTATGQR YFLNHIEKIT TWQDPRKAMN QPLNHMNLHP AVSSTPVPQR  180
SMAVSQPNLV MNHQHQQQMA PSTLSQQNHP TQNPPAGLMS MPNALTTQQQ QQQKLRLQRI  240
QMERERIRMR QEELMRQEAA LCRQLPMEAE TLAPVQAAVN PPTMTPDMRS ITNNSSDPFL  300
NGGPYHSREQ STDSGLGLGC YSVPTTPEDF LSNVDEMDTG ENAGQTPMNI NPQQTRFPDF  360
LDCLPGTNVD LGTLESEDLI PLFNDVESAL NKSEPFLTWL                        400

SEQ ID NO: 2           moltype = AA  length = 500
FEATURE                Location/Qualifiers
source                 1..500
                       mol_type = protein
                       organism = Homo sapiens
SEQUENCE: 2
MDPGQQPPPQ PAPQGQGQPP SQPPQGQGPP SGPGQPAPAA TQAAPQAPPA GHQIVHVRGD  60
SETDLEALFN AVMNPKTANV PQTVPMRLRK LPDSFFKPPE PKSHSRQAST DAGTAGALTP  120
QHVRAHSSPA SLQLGAVSPG TLTPTGVVSG PAATPTAQHL RQSSFEIPDD VPLPAGWEMA  180
KTSSGQRYFL NHIDQTTTWQ DPRKAMLSQM NVTAPTSPPV QQNMMNSASG PLPDGWEQAM  240
TQDGEIYYIN HKNKTTSWLD PRLDPRFAMN QRISQSAPVK QPPPLAPQSP QGGVMGGSNS  300
NQQQQMRLQQ LQMEKERLRL KQQELLRQAM RNINPSTANS PKCQELALRS QLPTLEQDGG  360
TQNPVSSPGM SQELRTMTTN SSDPFLNSGT YHSRDESTDS GLSMSSYSVP RTPDDFLNSV  420
DEMDTGDTIN QSTLPSQQNR FPDYLEAIPG TNVDLGTLEG DGMNIEGEEL MPSLQEALSS  480
DILNDMESVL AATKLDKESF                                              500

SEQ ID NO: 3           moltype = AA  length = 669
FEATURE                Location/Qualifiers
source                 1..669
                       mol_type = protein
                       organism = Homo sapiens
SEQUENCE: 3
MMRLRGSGML RDLLLRSPAG VSATLRRAQP LVTLCRRPRG GGRPAAGPAA AARLHPWWGG  60
GGWPAEPLAR GLSSSPSEIL QELGKGSTHP QPGVSPPAAP AAPGPKDGPG ETDAFGNSEG  120
KELVASGENK IKQGLLPSLE DLLFYTIAEG QEKIPVHKFI TALKSTGLRT SDPRLKECMD  180
MLRLTLQTTS DGVMLDKDLF KKCVQSNIVL LTQAFRRKFV IPDFMSFTSH IDELYESAKK  240
QSGGKVADYI PQLAKFSPDL WGVSVCTVDG QRHSTGDTKV PFCLQSCVKP LKYAIAVNDL  300
GTEYVHRYVG KEPSGLRFNK LFLNEDDKPH NPMVNAGAIV VTSLIKQGVN NAEKFDYVMQ  360
FLNKMAGNEY VGFSNATFQS ERESGDRNFA IGYYLKEKKC FPEGTDMVGI LDFYFQLCSI  420
EVTCESASVM AATLANGGFC PITGERVLSP EAVRNTLSLM HSCGMYDFSG QFAFHVGLPA  480
KSGVAGGILL VVPNVMGMMC WSPPLDKMGN SVKGIHFCHD LVSLCNFHNY DNLRHFAKKL  540
DPRREGGDQR VKSVINLLFA AYTGDVSALR RFALSAMDME QRDYDSRTAL HVAAAEGHVE  600
VVKFLLEACK VNPFPKDRWN NTPMDEALHF GHHDVFKILQ EYQVQYTPQG DSDNGKENQT  660
VHKNLDGLL                                                          669

SEQ ID NO: 4           moltype = AA  length = 598
FEATURE                Location/Qualifiers
source                 1..598
                       mol_type = protein
                       organism = Homo sapiens
SEQUENCE: 4
MMRLRGSGML RDLLLRSPAG VSATLRRAQP LVTLCRRPRG GGRPAAGPAA AARLHPWWGG  60
GGWPAEPLAR GLSSSPSEIL QELGKGSTHP QPGVSPPAAP AAPGPKDGPG ETDAFGNSEG  120
KELVASGENK IKQGLLPSLE DLLFYTIAEG QEKIPVHKFI TALKSTGLRT SDPRLKECMD  180
MLRLTLQTTS DGVMLDKDLF KKCVQSNIVL LTQAFRRKFV IPDFMSFTSH IDELYESAKK  240
QSGGKVADYI PQLAKFSPDL WGVSVCTVDG QRHSTGDTKV PFCLQSCVKP LKYAIAVNDL  300
GTEYVHRYVG KEPSGLRFNK LFLNEDDKPH NPMVNAGAIV VTSLIKQGVN NAEKFDYVMQ  360
FLNKMAGNEY VGFSNATFQS ERESGDRNFA IGYYLKEKKC FPEGTDMVGI LDFYFQLCSI  420
EVTCESASVM AATLANGGFC PITGERVLSP EAVRNTLSLM HSCGMYDFSG QFAFHVGLPA  480
KSGVAGGILL VVPNVMGMMC WSPPLDKMGN SVKGIHFCHD LVSLCNFHNY DNLRHFAKKL  540
DPRREGGDQR HSFGPLDYES LQQELALKET VWKKVSPESN EDISTTVVYR MESLGEKS    598

SEQ ID NO: 5           moltype = AA  length = 48
FEATURE                Location/Qualifiers
REGION                 1..48
                       note = Synthetic Construct
source                 1..48
                       mol_type = protein
                       organism = synthetic construct
SEQUENCE: 5
SVDDHFAKSL GDTWLQIGGS GNPKTANVPQ TVPMRLRKLP DSFFKPPE               48

SEQ ID NO: 6           moltype = AA  length = 24
```

-continued

```
FEATURE                 Location/Qualifiers
REGION                  1..24
                        note = Synthetic Construct; The first instance of Xaa =
                         F(3-Cl) which is a 3-chloro-phenylalanine; the second
                         instance of Xaa = Nle which is norleucine
VAR_SEQ                 6
VAR_SEQ                 13
source                  1..24
                        mol_type = protein
                        organism = synthetic construct
SEQUENCE: 6
PQTVPXAARL RKXABPASFF KPPE                                        24
```

COMPOSITIONS AND METHODS FOR ADMINISTERING A YAP1/WWRT1 INHIBITING COMPOSITION AND A GLS1 INHIBITING COMPOSITION

This Application is a continuation of U.S. application Ser. No. 16/765,977, filed on May 21, 2020, which is a national phase application filed under 35 U.S.C. § 371 of PCT International Application No. PCT/US2018/062013, filed on Nov. 20, 2018, which claims the benefit of U.S. Provisional Application No. 62/589,706, filed on Nov. 22, 2017, the disclosures of which are incorporated herein by reference in their entirety.

This invention was made with government support under Grant No. R01 HL124021 awarded by the National Institute of Health. The Government has certain rights in the invention.

INCORPORATION-BY-REFERENCE OF MATERIAL SUBMITTED ELECTRONICALLY

Incorporated by reference in its entirety herein is a computer-readable amino acid sequence listing submitted concurrently herewith and identified as follows: One 9.771 bytes ST26 file named "10504-023US2_ST26.xml", created on Nov. 30, 2023.

REFERENCE TO SEQUENCE LISTING

The Sequence Listing submitted Jul. 11, 2023, as an .XML file titled "10504-023US2.xml", created on Jul. 11, 2023, and having a size of 10,215 bytes is hereby incorporated by reference pursuant to 37 C.F.R. § 1.52(e)(5).

I. BACKGROUND

Pulmonary hypertension (PH)) and its particularly severe subtype pulmonary arterial hypertension (PAH) are a poorly understood vascular diseases with increasing prevalence worldwide but with inadequate treatment options. There exist over a dozen approved vasodilator drugs for treatment of this disease; nonetheless, mortality with current therapies remains high. At the cellular and molecular levels in the diseased pulmonary vasculature, PH is characterized by metabolic dysregulation, pro-proliferative states, and adverse pulmonary vascular remodeling and stiffness. As such, there have been recent efforts to develop novel pharmacologic approaches that target the molecular origins of PH and thus could represent disease-modifying opportunities. Nevertheless, what are needed are improved treatments of pulmonary disease.

II. SUMMARY

Disclosed are particles comprising a YAP1/WWTR1 inhibiting agent and a glutaminase inhibiting agent and methods of their use.

In one aspect, disclosed herein are therapeutic particles (such as, for example, a poly(lactic-co-glycolic) acid (PLGA)) particle comprising a biocompatible polymer, a YAP1/WWRT1 inhibiting agent (such as, for example, verteporfin) and a glutaminase inhibiting agent (such as, for example, CB-839 and/or C968).

Also disclosed herein are the therapeutic particle of any preceding aspect, wherein the YAP1/WWRT1 inhibiting agent and glutaminase inhibiting agent are released from the particle in about 1 day to about 3 days after administration to a subject.

In one aspect, disclosed herein are methods of treating a pulmonary disease (such as, for example, pulmonary vascular disease, pulmonary hypertension, pulmonary arterial hypertension, pulmonary stiffness, pulmonary fibrosis, chronic obstructive pulmonary disease (COPD), cystic fibrosis, emphysema, asthma, pulmonary embolism, acute lung disease, sepsis, tuberculosis, sarcoidosis, pulmonary inflammation due to microbial infection (such as, for example, pneumonia and influenza), or lung cancer (such as small cell lung cancer and non-small cell lung cancer) in a subject in need of such treatment comprising administering the therapeutic particle of any preceding aspect to the subject.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows the local inhibition of YAP1/WWRT1 and glutaminase pathways for effective amelioration of PH.

Figure 2A:
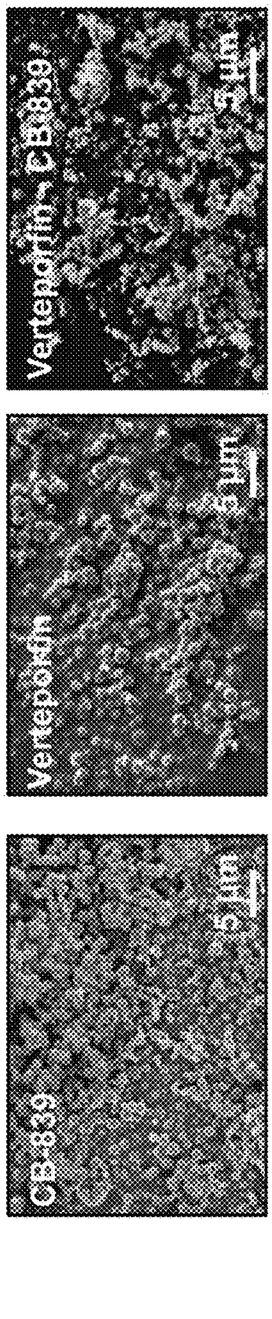
Figure 2B:
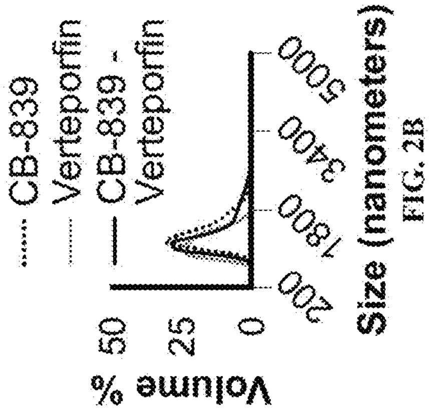
Figure 2C:
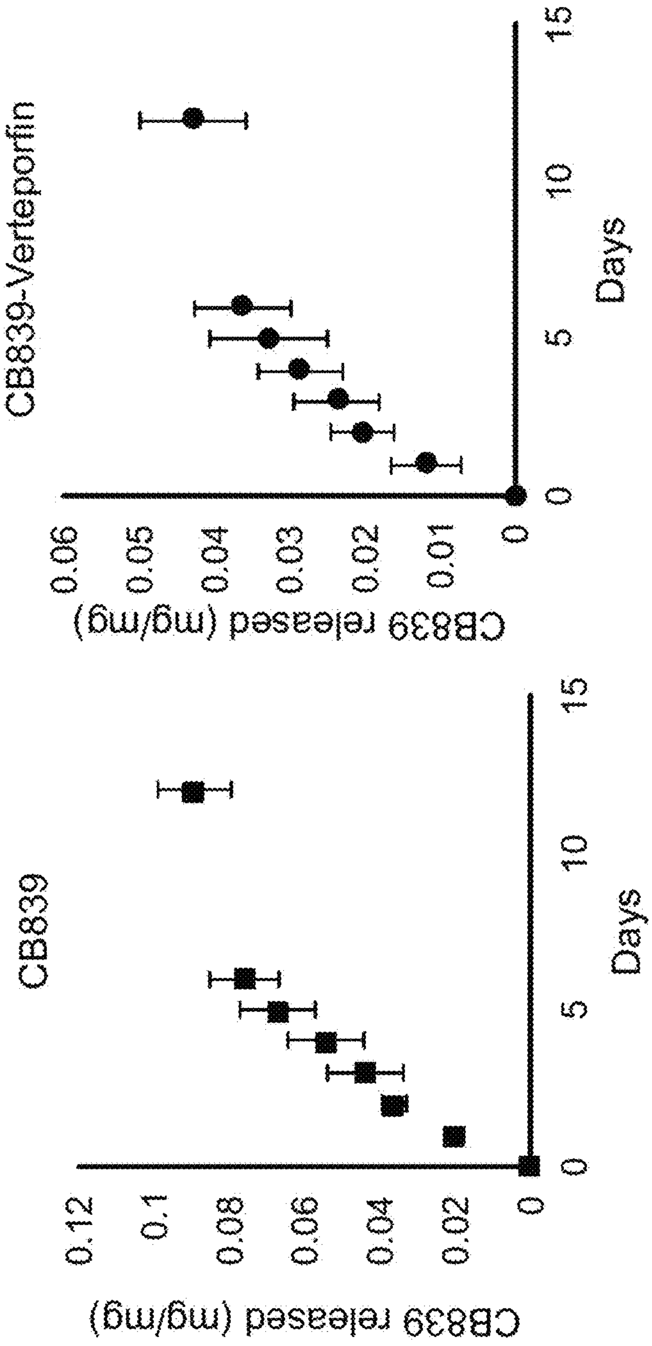
Figure 2D:
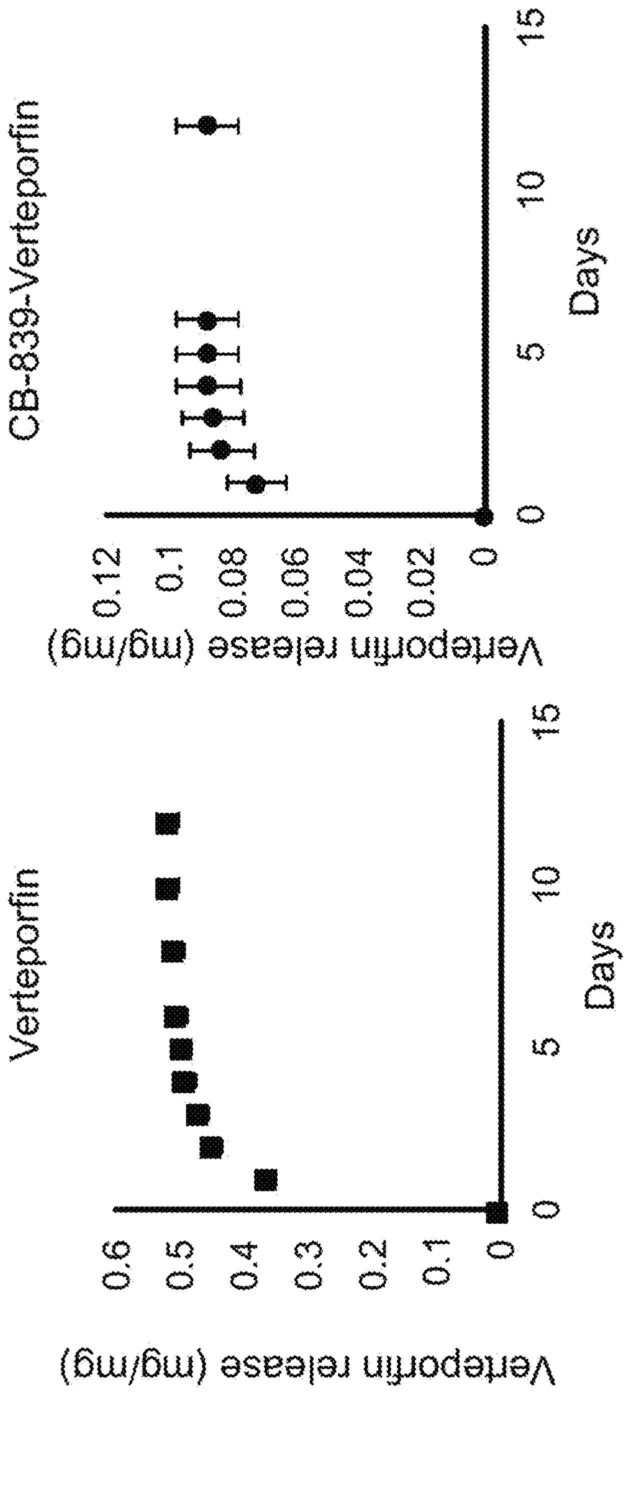

FIGS. 2A, 2B, 2C, and 2D show that PLGA microparticles are within a size range for inhalation and release verteporfin and CB-839 in a sustained manner. FIG. 2A shows scanning electron microscope images of CB-839 alone encapsulated, verteporfin alone encapsulated, and CB-839 with verteporfin encapsulated microparticles show smooth surface morphology. FIG. 2B shows size distribution of the microparticles obtained from dynamic light scattering experiments, indicates that the average microparticle size for all the microparticles is approximately 1 μm. FIG. 2C shows release kinetics of CB-839 from PLGA microparticles encapsulating CB-839-verteporfin or encapsulating CB-839 only. FIG. 2D shows release kinetics of verteporfin from PLGA microparticles encapsulating CB-839-verteporfin or encapsulating verteporfin only.

Figure 3:
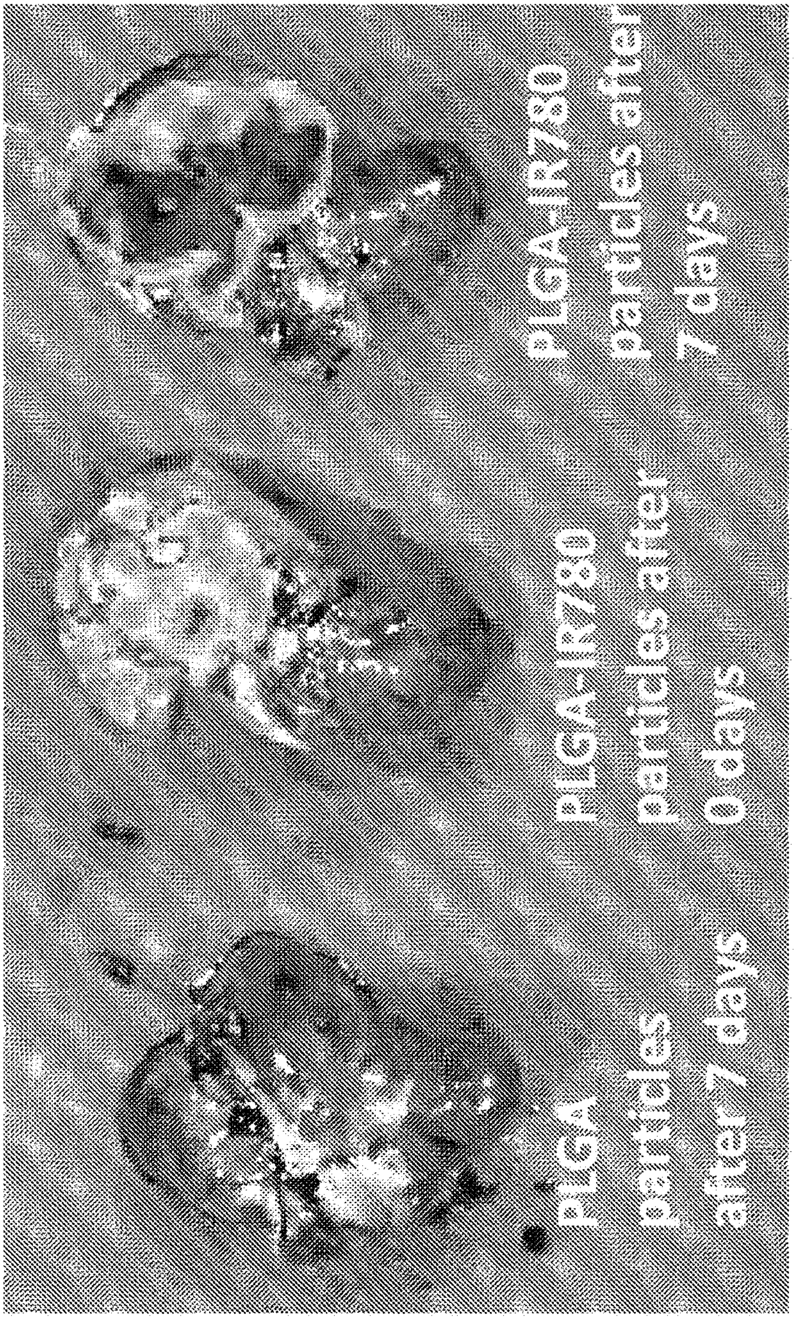

FIG. 3 shows that PLGA microparticles deliver payload into the lungs of rats. Fluorescence image of the lungs of rats after intra-tracheal administration with PLGA microparticles encapsulating near infrared dye IR780 versus no dye, imaged on day 0 and day 7 post-administration.

FIGS. 4A, 4B, 4C, and 4D show delivery of verteporfin and CB-839 simultaneously in vivo improves hemodynamic manifestations of PH in monocrotaline-exposed rats. FIG. 4A shows a study design for the induction of PH using monocrotaline (MCT) via intraperitoneal (i.p.) injection followed by administration of microparticles (i.t.=intra-tracheal) for treatments. FIG. 4B shows that PLGA microparticles delivering verteporfin (Vert) and CB-839 significantly decreases Fulton index (RV/LV+S mass) and right ventricular systolic pressure (RVSP) as compared to the control of blank microparticles. FIG. 4C shows PLGA microparticles delivering verteporfin (Vert) alone significantly decreases Fulton index, and RVSP could not be compared due to death of rats. FIG. 4D shows PLGA microparticles delivering CB-839 alone does not significantly decreased Fulton index or RVSP as compared to the control of blank microparticles.

Figure 5A:
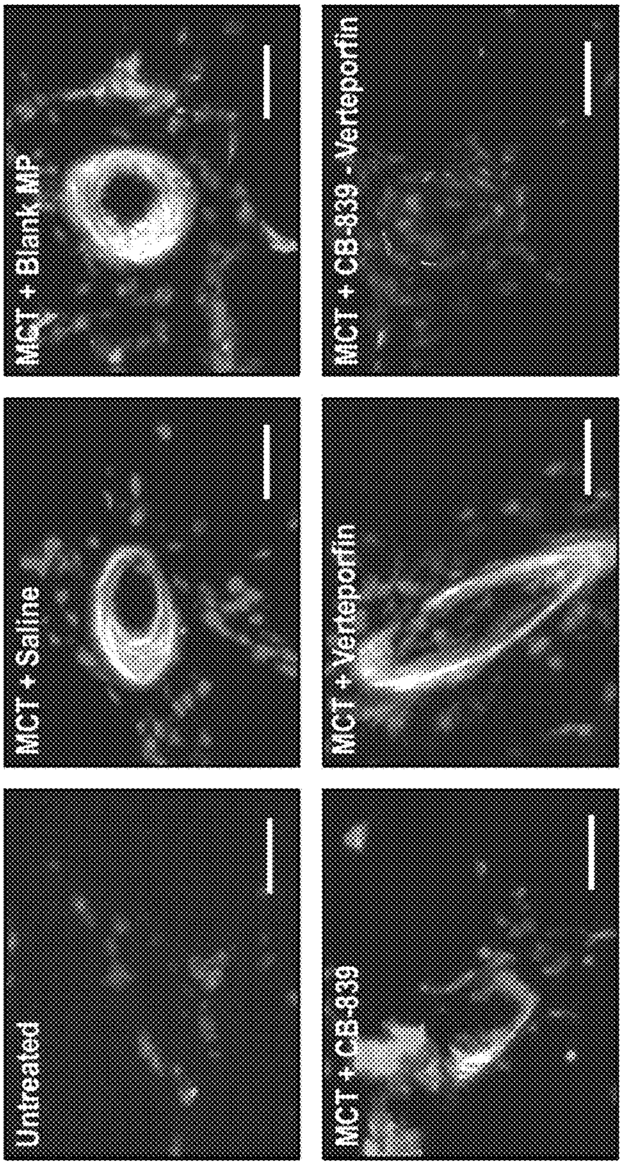
Figure 5B:
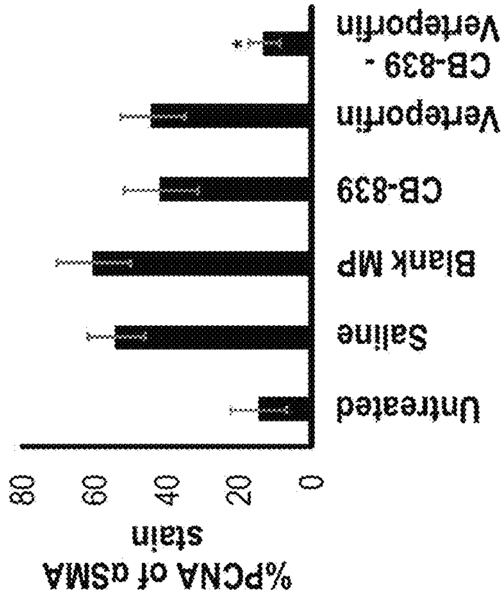
Figure 5C:
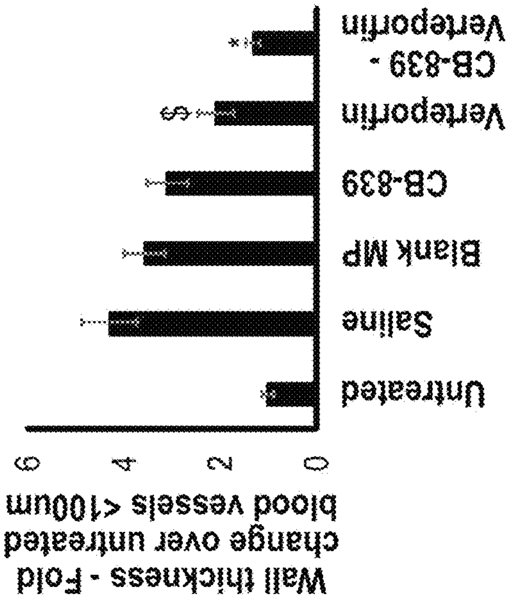

FIGS. 5A, 5B, and 5C show simultaneous pharmacologic inhibition of GLS1 and YAP1/WWRT1 in monocrotaline-exposed rats decreases pulmonary vascular cell proliferation and pulmonary vascular remodeling. FIG. 5A shows representative images of small pulmonary arterioles (<10 μm diameter) of the lungs (blue—nuclei; red—PCNA; green—

α-SMA; scale bar=20 μm). FIG. 5B shows the percentage of PCNA of α-SMA positive vascular cells in the CB-839 and verteporfin combination group is significantly lower than negative controls of saline and blank microparticles (MP) and significantly different than single drug treatments alone (n=5-12; ±SEM; *-p<0.05 with all the conditions except untreated). FIG. 5C shows that as normalized to untreated group, the wall thickness of vessels in the verteporfin+CB-839 combination treatment group is significantly lower than either single drug treatment or negative controls of saline and blank microparticles (MP) (n=10-12 vessels; ±SEM; *-p<0.05 with all the conditions except untreated; $-p<0.05 with all the conditions).

Figure 6A:
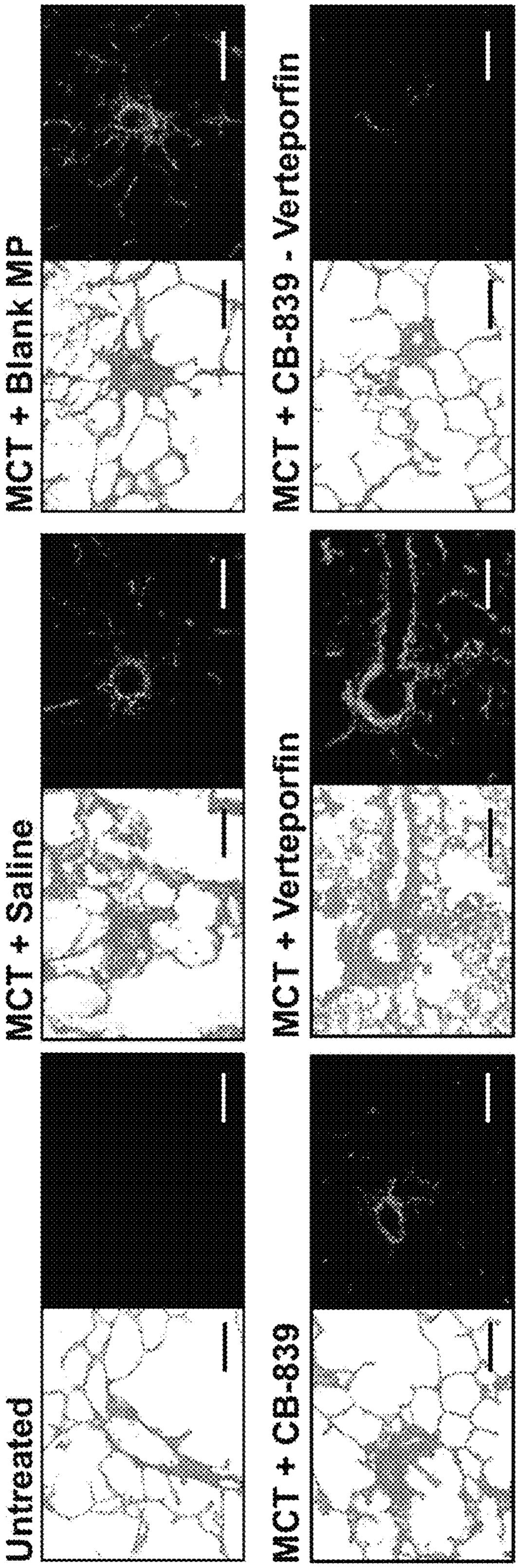
Figure 6B:
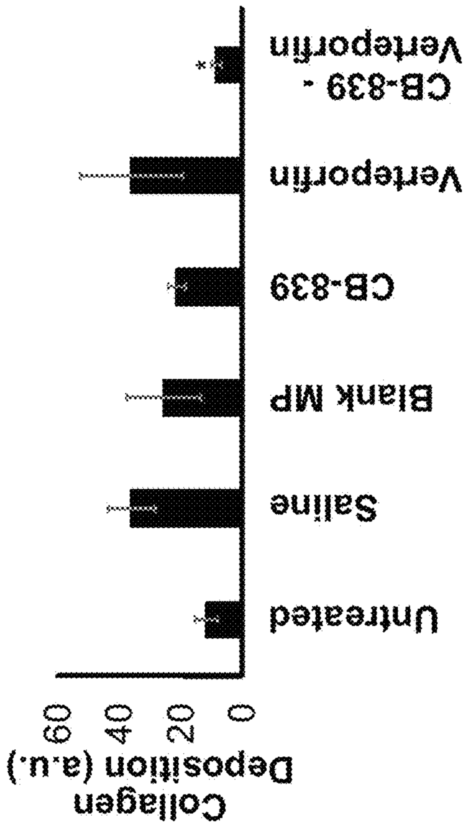
Figure 6C:
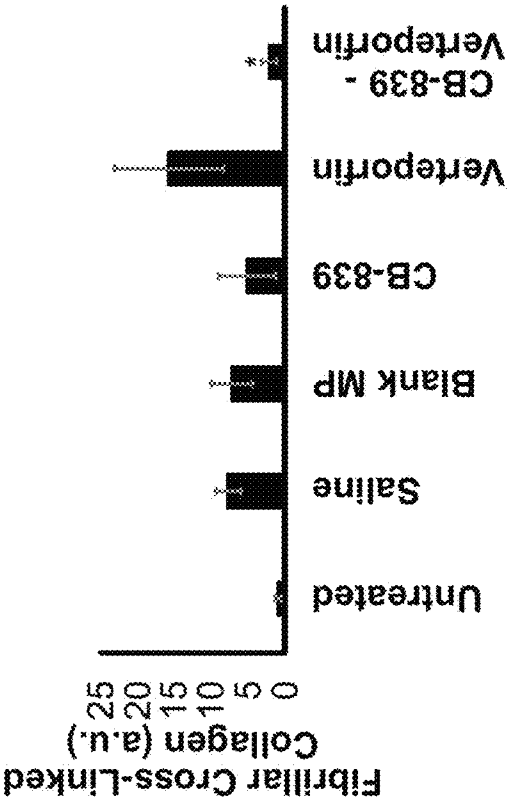

FIGS. 6A, 6B, and 6C show simultaneous pharmacologic inhibition of GLS1 and YAP1/WWRT1 in MCT-exposed rats decreases collagen deposition and collagen crosslinking in pulmonary arterioles. FIG. 6A shows representative images of picrosirius red stain of lung tissues, showing fibrillar collagen deposition (red—bright field) and cross-linked fibrillar collagen assembly (red—collagen type I, and green—collagen type III, using orthogonal polarized images, scale bar=40 μm). FIG. 6B shows the quantification of the % area of picrosirius red stain under non-polarized light (represented as arbitrary units—a.u.) shows that the CB-839 and verteporfin combination significantly decreases pulmonary arteriolar collagen deposition as compared with negative controls of saline and blank microparticles (MP) and is significantly different than single drug treatment alone (n=6-10; ±SEM; *-p<0.05 with all the conditions except untreated). FIG. 6C shows the quantification of the % area of picrosirius red stain under polarized light (represented as arbitrary units—a.u.). FIG. 6C shows that the CB-839 and verteporfin combination group significantly decreases pulmonary arteriolar cross-linked collagen as compared with negative controls of saline and blank microparticles (MP) and is significantly different than verteporfin alone treatment (n=6-10; ±SEM; *-p<0.05 with all the conditions except untreated and CB-839).

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

"Biocompatible" generally refers to a material and any metabolites or degradation products thereof that are generally non-toxic to the recipient and do not cause significant adverse effects to the subject.

A "composition" is intended to include a combination of active agent or agents (for example, a verteporfin, a C968 and/or CB-839 composition) and another compound or composition, inert (for example, a detectable agent or label) or active, such as an adjuvant.

A "control" is an alternative subject or sample used in an experiment for comparison purposes. A control can be "positive" or "negative."

"Controlled release" or "sustained release" refers to release of an agent from a given dosage form in a controlled fashion in order to achieve the desired pharmacokinetic profile in vivo. An aspect of "controlled release" agent delivery is the ability to manipulate the formulation and/or dosage form in order to establish the desired kinetics of agent release.

"Polymer" refers to a relatively high molecular weight organic compound, natural or synthetic, whose structure can be represented by a repeated small unit, the monomer. Non-limiting examples of polymers include polyethylene, rubber, cellulose. Synthetic polymers are typically formed by addition or condensation polymerization of monomers. The term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc. as well as pharmaceutically acceptable, pharmacologically active salts, esters, amides, proagents, conjugates, active metabolites, isomers, fragments, analogs, etc.

As used herein, "modulate" means to effectuate a change (either an increase or a decrease) in the amount of gene expression, protein expression, amount of a symptom, disease, composition, condition, or activity.

An "increase" can refer to any change that results in a greater gene expression, protein expression, amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller gene expression, protein expression, amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

In some instances, a desired biological or medical response is achieved following administration of multiple dosages of the composition to the subject over a period of days, weeks, or years. The terms "pharmaceutically effective amount," "therapeutically effective amount," or "therapeutically effective dose" include that amount of a composition such as a YAP1/WWRT1 inhibiting composition and/or a glutaminase inhibiting composition, that, when administered, is sufficient to prevent development of, or alleviate to some extent, one or more of the symptoms of the disease being treated. The therapeutically effective amount will vary depending on the composition such as a YAP1/WWRT1 inhibiting composition and/or a glutaminase inhibiting composition, the disease and its severity, the route of administration, time of administration, rate of excretion, drug combination, judgment of the treating physician, dosage form, and the age, weight, general health, sex and/or diet of the subject to be treated. In the context of the present method, a pharmaceutically or therapeutically effective amount or dose of a YAP1/WWRT1 inhibiting composition and/or a glutaminase inhibiting composition, includes an amount that is sufficient to treat pulmonary hypertension, pulmonary arterial hypertension and/or pulmonary vascular stiffness.

The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

The term "pulmonary vascular disease" is used herein to refer to pulmonary vascular hypertension and includes both pulmonary hypertension (PH) and pulmonary arterial hypertension (PAH). Pulmonary vascular disease can be caused by or includes pulmonary vascular stiffness.

By "salt" is meant zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Lists of suitable salts are found in Remington's Pharmaceutical Sciences, 20th ed., Lippincott Williams & Wilkins, Baltimore, MD, 2000, p. 704; and "Handbook of Pharmaceutical Salts: Properties, Selection, and Use," P. Heinrich Stahl and Camille G. Wermuth, Eds., Wiley-VCH, Weinheim, 2002. Example of salts include, but are not limited to, mineral or organic acid salts of basic residues such as amines; and alkali or organic salts of acidic residues such as carboxylic acids.

Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, sodium, potassium, magnesium, and calcium salts of the compounds disclosed herein, and the like can be formed.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

By "prodrug" is meant compounds which, under physiological conditions, are converted into a therapeutically active compound. Prodrugs are administered in an inactive (or significantly less active) form. Once administered, the prodrug is metabolized in the body (in vivo) into the active compound. Certain compounds disclosed herein can also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they can be easier to administer than the compound, or parent drug. They can, for instance, be bioavailable by oral administration whereas the parent drug is not. The prodrug can also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, Design of Prodrugs, Elsevier, 1985; and Bioreversible Carriers in Drug Design, ed. Edward Roche, American Pharmaceutical Association and Pergamon Press, 1987. Prodrugs of the active compound can be conventional esters. Some common esters which have been utilized as prodrugs are phenyl esters, aliphatic ($C_7$-$C_8$ or $C_8$-$C_{24}$) esters, cholesterol esters, acyloxymethyl esters, carbamates, and amino acid esters. Preferably, prodrugs of the compounds disclosed herein are pharmaceutically acceptable.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more (e.g., referred to as "disubstitued," "trisubstituted," and the like) and the same or different for appropriate organic compounds. For purposes of this disclosure, the heteroatoms, such as nitrogen and oxygen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Also, as used herein "substitution" or "substituted with" is meant to encompass configurations where one substituent is fused to another substituent. For example, an aryl group substituted with an aryl group (or vice versa) can mean that one aryl group is bonded to the second aryl group via a single sigma bond and also that the two aryl groups are fused, e.g., two carbons of one alkyl group are shared with two carbons of the other aryl group.

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular therapeutic particle is disclosed and discussed and a number of modifications that can be made to a number of molecules including the therapeutic particle are discussed, specifically contemplated is each and every combination and permutation of therapeutic particle and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Pulmonary hypertension (PH) is a poorly understood vascular disease with increasing prevalence worldwide and 5 major World Health Organization classifications (WHO PH Groups 1-5) but with inadequate treatment options. There exist over a dozen approved vasodilator drugs for treatment of this disease; nonetheless, mortality with current therapies remains high. At the cellular and molecular levels in the diseased pulmonary vasculature, PH is characterized by metabolic dysregulation, pro-proliferative states, and adverse pulmonary vascular remodeling and stiffness. As such, there have been recent efforts to develop novel pharmacologic approaches that target the molecular origins of PH and thus could represent disease-modifying opportunities. Herein is shown that a key molecular connection between vessel stiffness and metabolic dysregulation that promotes PH. Namely, it was found that vessel stiffness mechanoactivates the YAP1/WWRT1 co-transcription factors to induce glutaminolysis via induction of glutaminase (GLS1 and/or GLS2), thus sustaining the metabolic needs of proliferating pulmonary vascular cells and driving PH in vivo.

The molecular insights disclosed herein advanced the paradigm of vascular stiffness beyond merely a consequence of long-standing vascular dysfunction but rather as a specific metabolic cause of vascular cell proliferation and PH development. Importantly, it was demonstrated substantial reversal of PH in a monocrotaline rat model of PH by pharmacologic inhibitors of YAP1 (verteporfin) and/or glutaminase (CB-839 and/or C968). When delivered systemically, these drugs improved the hemodynamic and histopathologic manifestations of PH by decreasing the hyperproliferative phenotypes of diseased vascular cells. Accordingly, disclosed herein are compositions therapeutic nanoparticles comprising a biocompatible polymer, a YAP1/WWRT1 inhibiting agent (such as, for example, verteporfin) and a glutaminase (including, but not limited to GLS1 and/or GLS2) inhibiting agent including, but not limited to CB-839 and/or C968 or any salt, prodrug, or derivative of CB-839 or C968.

As noted above, the therapeutic particles comprise a YAP1/WWTR1 inhibiting agent. Yes-associated protein (YAP1 also referred to herein as YAP) and its homolog WWRT1 (also known as WW domain-containing transcription regulator protein 1 (see SEQ ID NO: 2) and sometimes referred to as TAZ) are transcriptional regulators that regulates of cell proliferation and suppressing apoptotic genes. In some embodiments, the WWRT1 polynucleotide encodes an WWRT1 polypeptide comprising the sequence of SEQ ID NO: 1, or a polypeptide sequence having at or greater than about 80%, at or greater than about 85%, at or greater than about 90%, at or greater than about 95%, or at or greater than about 98% homology with SEQ ID NO: 1, or a polypeptide comprising a portion of SEQ ID NO: 1. The WWRT1 polypeptide of SEQ ID NO: 1 may represent an immature or pre-processed form of mature WWRT1, and accordingly, included herein are mature or processed portions of the WWRT1 polypeptide in SEQ ID NO:1.

The term "YAP" refers herein to a YAP polypeptide also known as YAP1, Yes-associated protein 1, or Yap65 and in humans, is encoded by the YAP1 gene. The term "YAP polynucleotide" refers to a YAP encoding polynucleotide and includes a YAP1 gene in its entirety or a fragment thereof. In some embodiments, the YAP polypeptide or polynucleotide is that identified in one or more publicly available databases as follows: HGNC: 16262; Entrez Gene: 10413; Ensembl: ENSG00000137693; OMIM: 606608; and UniProtKB: P46937. In some embodiments, the YAP polynucleotide encodes an YAP polypeptide comprising the sequence of SEQ ID NO: 2, or a polypeptide sequence having at or greater than about 80%, at or greater than about 85%, at or greater than about 90%, at or greater than about 95%, or at or greater than about 98% homology with SEQ ID NO: 2, or a polypeptide comprising a portion of SEQ ID NO: 2. The YAP polypeptide of SEQ ID NO: 2 may represent an immature or pre-processed form of mature YAP, and accordingly, included herein are mature or processed portions of the YAP polypeptide in SEQ ID NO: 2.

The term "YAP1/WWRT1 inhibiting agent" refers herein to any composition that when administered to a subject or vascular cell, decreases expression and/or inactivates a constituent in a YAP1 and/or a WWRT1. In some embodiments, the term "YAP1/WWRT1 inhibiting agent" refers herein to any composition that when administered to a subject or vascular cell and decreases or inactivates YAP1 and/or WWRT1 and results in reduced pulmonary hypertension, pulmonary arterial hypertension and/or vascular stiffness. As used herein a YAP1/WWRT1 inhibiting agent (i.e., a YAP1/WWRT1 inhibitor) comprises any small molecule, peptide, protein, antibody, and/or functional nucleic acid (siRNA, RNA, aptamer) that inhibits transcriptional function of YAP1/WWRT1. Examples of YAP1/WWRT1 inhibitors include, but are not limited to verteporfin, XMU-MP-1 (4-((5,10-dimethyl-6-oxo-6,10-dihydro-5H-pyrimido[5,4-b]thieno[3,2-e][1,4]diazepin-2-yl)amino)benzenesulfonamide), Super-TDU (SVDDHFAKSLGDTWLQIGGSGNPKTANVPQTVPMRLRKLPDSFFKPPE (SEQ ID NO: 5)), peptide 17 PQTVPF(3-C1)RLRK Nle PASFFKPPE (SEQ ID NO: 6), CA3 (shown below),

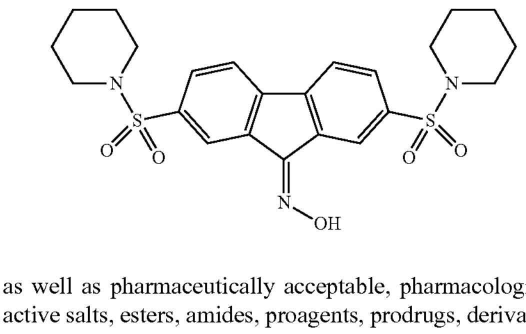

as well as pharmaceutically acceptable, pharmacologically active salts, esters, amides, proagents, prodrugs, derivatives, conjugates, active metabolites, isomers, fragments, and/or analogs thereof.

The term "verteporfin" refers herein to a chemical composition having the chemical name 3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.$1^{3,6}$.$1^{8,11}$.$1^{13,16}$.$0^{19,24}$]octacosa-1,3,5,7,9,11(27),12,14,16,18(25),19,21-dodecaen-9-yl]propanoic acid, having the chemical structure as shown below, and/or as described in U.S. Pat. Nos. 5,707,608, 5,798,345, and/or 5,756,541.

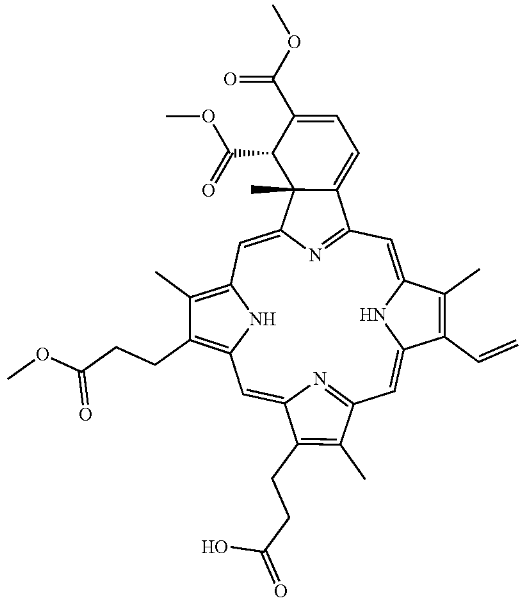 [SMILES: C=Cc1c(C)c2cc3nc(cc4[nH]c(cc5nc(cc1[nH]2)C(C)=C5CCC(=O)O)c(CCC(=O)OC)c4C)[C@@]1(C)C3=CC=C(C(=O)OC)[C@H]1C(=O)OC]

Glutaminase (including, but not limited to GLS1 and/or GLS2) also known as K-glutaminase in humans, is encoded by the GLS gene. The term "GLS1 polynucleotide" refers to a GLS1 encoding polynucleotide and includes a GLS gene in its entirety or a fragment thereof. In some embodiments, the GLS1 polypeptide or polynucleotide is that identified in one or more publicly available databases as follows: HGNC: 4331; Entrez Gene: 2744; Ensembl: ENSG00000115419; OMIM: 138280; and UniProtKB: 094925. In some embodiments, the GLS1 polynucleotide encodes an GLS1 polypeptide comprising the sequence of SEQ ID NO: 3 (known as the KGA isoform), or a polypeptide sequence having at or greater than about 80%, at or greater than about 85%, at or greater than about 90%, at or greater than about 95%, or at or greater than about 98% homology with SEQ ID NO: 3, or a polypeptide comprising a portion of SEQ ID NO: 3. The GLS1 polypeptide of SEQ ID NO: 3 may represent an immature or pre-processed form of mature WWRT1, and accordingly, included herein are mature or processed portions of the GLS polypeptide in SEQ ID NO: 3. In some examples, the GLS1 polypeptide is the GAC isoform wherein its sequence differs from SEQ ID NO:3 as set forth in SEQ ID NO: 4 and as follows: 551-669: VKSVINLLFA . . . TVHKNLDGLL→HSFGPLDYES . . . YRMESLGEKS.

The disclosure herein provides for a particle comprising in one aspect a glutaminase inhibiting agent, a glutaminase inhibitor. The term "glutaminase inhibiting agent" refers herein to any composition that when administered to a subject or vascular cell, decreases or inactivates (partially or wholly) a GLS1. In some embodiments, the term "glutaminase inhibiting agent" refers herein to any composition that when administered to a subject or vascular cell and decreases or inactivates a GLS1 also treats pulmonary hypertension, pulmonary arterial hypertension and/or vascular stiffness. Non-limiting examples of glutaminase inhibiting compositions are CB-839; C968; 6-Diazo-5-oxo-L-norleucine (DON); BPTES (N,N'-[thiobis(2,1-ethanediyl-1, 3,4-thiadiazole-5,2-diyl)]bis-benzeneacetamide); 2-Phenyl-N-(5-{4-[5-(2-phenylacetamido)-1,3,4-thiadiazol-2-yl] piperazin-1-yl}-1,3,4-thiadiazol-2-yl)acetamido; 2-Phenyl-N-{5-[1-(5-phenylacetylamino-[1,3,4]thiadiazol-2-yl)-piperidin-4-yloxy]-[1,3,4]thiadiazol-2-yl}-acetamide; N-{5-[1-(5-Acetylamino-[1,3,4]thiadiazol-2-yl^acetamide; 2-Phenyl-N-[5-({1-[5-(2-phenylacetamido),3,4-thiadiazol-2-yl] azetidin-3-yl}oxy)-1,3,4-thiadiazol-2-yl]acetamido; N-{5-[1-(5-Amino-[1,3,4]thiadiazol-2-yl)-piperidin-4-yloxy]-[1,3,4]thiadiazol-2-yl}-2-phenyl-acetamide; N-(5-{[1-(5-amino-1,3,4-thiadiazol-2-yl)azetidin-3-yl]amino}-1,3,4-thiadiazol-2-yl)-2-phenylacetamide; 2-(Pyridin-3-yl)-N-(5-(4-((5-(2-(pyridin-3-yl)acetamido)-1,3,4-thiadiazol-2-yl) oxy)piperidin-1-yl)-1,3,4-thiadiazol-2-yl)acetamido; 2-Cyclopropyl-N-(5-(4-((5-(2-cyclopropylacetamido)-1,3,4-thiadiazol-2-yl)oxy)piperidin-1-yl)-1,3,4-thiadiazol-2-yl) acetamido; 2-Phenyl-N-{6-[1-(6-phenylacetylamino-pyridazin-3-yl)-piperidin-4-yloxy]-pyridazin-3-yl}-acetamide; 2-Phenyl-N-(5-(4-((5-(2-phenylacetamido)-1,3,4-thiadiazol-2-yl)amino)piperidin-1-yl)-1,3,4-thiadiazol-2-yl)acetamido; (R)-2-Phenyl-N-(5-(3-((5-(2-phenylacetamido)-1,3,4-thiadiazol-2-yl)amino)pyrrolidin-1-yl)-1,3,4-thiadiazol-2-yl)acetamido; N-(5-{R3S)-1-(5-acetamido-1,3,4-thiadiazol-2-yl)pyrrolidin-3-yl]amino}-1,3,4-thiadiazol-2-yl)acetamido; N-(5-{[(3R)-1-(5-acetamido-1,3,4-thiadiazol-2-yl)pyrrolidin-3-yl]amino}-1,3,4-thiadiazol-2-yl)acetamido; 2-Phenyl-N-(5-{[(3R)-1-[5-(2-phenylacetamido)-1,3,4-thiadiazol-2-yl]pyrrolidin-3-yl] oxy}-1,3,4-thiadiazol-2-yl)acetamido; 2-Phenyl-N-(5-(3-((5-(2-phenylacetamido)-1,3,4-thiadiazol-2-yl)oxy) piperidin-1-yl)-1,3,4-thiadiazol-2-yl)acetamido; N-(5-{[(3R)-1-(5-amino-1,3,4-thiadiazol-2-yl)pyrrolidin-3-yl] oxy}-1,3,4-thiadiazol-2-yl)-2-phenylacetamide; 2-Phenyl-N-{5-[(3S)-3-({[5-(2-phenylacetamido)-1,3,4-thiadiazol-2-yl]oxy}methyl)pyrrolidin-1-yl]-1,3,4-thiadiazol-2-yl}acetamido; 2-phenyl-N-{5-[(3R)-3-({[5-(2-phenylacetamido)-1,3,4-thiadiazol-2-yl]oxy}methyl) pyrrolidin-1-yl]-1,3,4-thiadiazol-2-yl}acetamido; (+)-(anti)-2-Phenyl-N-{5-[3-(5-phenylacetylamino-[1,3,4]thiadiazol-2-ylamino)-cyclopentylaminol-[1,3,4]thiadiazol-2-yl}-acetamide; 2-Phenyl-N-{6-[1-(5-phenylacetylamino-[1,3,4] thiadiazol-2-yl)-piperidin-4-yloxy]-pyridazin-3-yl}-acetamide; N-(6-{1-[5-(2-Pyridin-2-yl-acetylamino)-[1,3,4] thiadiazol-2-yl]-piperidin-4-yloxy}-pyridazin-3-yl)-2-(3-trifluoromethoxy-phenyl)-acetamide; 2-Phenyl-N-{5-[1-(5-phenylacetylamino-[1,3,4]thiadiazol-2-yl)-piperidin-4-ylmethoxy]-[1,3,4]thiadiazol-2-yl}-acetamide; (S)-2-Phenyl-N-(5-(3-((5-(2-phenylacetamido)-1, 3,4-thiadiazol-2-yl)amino)pyrrolidin-1-yl)-1, 3, 4-thiadiazol-2-yl) acetamido; (S)-2-Phenyl-N-(5-(3-((5-(2-phenylacetamido)-1,3,4-thiadiazol-2-yl)oxy)pyrrolidin-1-yl)-1,3,4-thiadiazol-2-yl}acetamido; N-(5-((1-(5-amino-1, 3, 4-thiadiazol-2-yl) azetidin-3-yl) oxy)-1, 3, 4-thiadiazol-2-yl)-2-phenylacetamide; 2-(Pyridin-2-yl)-N-{5-[(1-{5-[2-(pyridin-2-yl)acetamido]-1,3,4-thiadiazol-2-yl}piperidin-4-yl)amino]-1,3,4-thiadiazol-2-yl}acetamido; 2-(Pyridin-3-yl)-N-{5-[(1-{5-[2-(pyridin-3-yl)acetamido]-1,3,4-thiadiazol-2-yl}piperidin-4-yl)amino]-1,3,4-thiadiazol-2-yl}acetamido; 2-(Pyridin-2-yl)-N-{5-[(1-{5-[2-(pyridin-2-yl)acetamido]-1,3,4-thiadiazol-2-yl}piperidin-4-yl)oxy]-1,3,4-thiadiazol-2-yl}acetamido; 2-(Pyridin-4-yl)-N-{5-[(1-{5-[2-(pyridin-4-yl)acetamido]-1,3,4-thiadiazol-2-yl}piperidin-4-yl) amino]-1,3,4-thiadiazol-2-yl}acetamido; 2-Cyclopropyl-N-[5-(4-{[5-(2-phenylacetamido)-1,3,4-thiadiazol-2-yl] amino}piperidin-1-yl)-1,3,4-thiadiazol-2-yl]acetamido; or any other glutaminase inhibitor having formula A as set forth in U.S. patent application Ser. No. 15/516,002, filed on Jan. 10, 2015, which is incorporated herein by reference in its entirety for the teachings of glutaminase inhibitors and as shown below:

Formula A

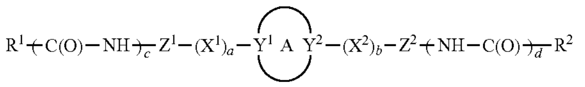

wherein A is a ring;

$Y^1$ and $Y^2$ are each independently N or C with the proper valency;

$X^1$ and $X^2$ are each independently —NH—, —O—, —$CH_2$—O—, —NH—$CH_2$—, or —N($CH_3$)—$CH_2$—, provided that when at least one of $X^1$ and $X^2$ is —$CH_2$—O—, —NH—$CH_2$—, or —N(CH)—$CH_2$— then the —$CH_2$— is directly connected to A;

a and b are each independently 0 or 1;

c and d are each independently 0 or 1;

$Z^1$ and $Z^2$ are each independently a heterocyclic; and $R^1$ and $R^2$ are each independently optionally substituted alkyl, optionally substituted aralkyl, optionally substituted cycloalkyl, amino, optionally substituted heteroaralkyl, optionally substituted alkylalkoxy, optionally substituted alkylaryloxy, optionally substituted aryl, optionally substituted heteroaryl, or optionally substituted heterocycloalkyl;

provided that if $Y^1$ and $Y^2$ are each C, then a is 1 and b is 1;

provided that if $Y^1$ and $Y^2$ are each N, then a is 0 and b is 0;

provided that if $Y^1$ is N and $Y^2$ is C, then a=0 and b=1;

provided that if $Y^1$ is C and $Y^2$ is N, then a=1 and b=0;

provided that if c=0 and d=0, then $R^1$ and $R^2$ are both amino;

provided that if c is 1 and d is 1, then both $R^1$ and $R^2$ are not amino;

provided that if c is 0 and d is 1, then $R^1$ is amino and $R^2$ is optionally substituted alkyl, optionally substituted aralkyl, optionally substituted cycloalkyl, optionally substituted heteroaralkyl, optionally substituted alkylalkoxy, optionally substituted alkylaryloxy, optionally substituted aryl, optionally substituted heteroaryl, or optionally substituted heterocycloalkyl; and provided that if c is 1 and d is 0, then $R^2$ is amino and $R^1$ is optionally substituted alkyl, optionally substituted aralkyl, optionally substituted cycloalkyl, optionally substituted heteroaralkyl, optionally substituted alkylalkoxy, optionally substituted alkylaryloxy, optionally substituted aryl, optionally substituted heteroaryl, or optionally substituted heterocycloalkyl; as well as pharmaceutically acceptable, pharmacologically active salts, esters, amides, proagents, prodrugs, derivatives, conjugates, active metabolites, isomers, fragments, and/or analogs of any of the glutaminase inhibitors disclosed herein.

The term "C968" refers herein to a chemical composition having the chemical structure as shown below and/or having the name 5-(3-Bromo-4-(dimethylamino)phenyl)-2,2-dimethyl-2,3,5,6-tetrahydrobenzo[a]phenanthridin-4(1H)-one.

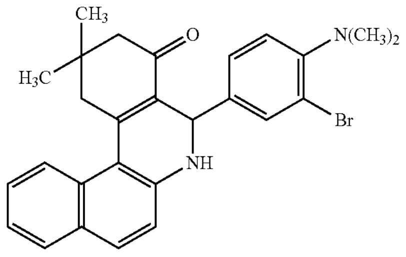 [SMILES: CN(C)c1ccc(C2Nc3ccc4ccccc4c3C3=C2C(=O)CC(C)(C)C3)cc1Br]

The term "CB-839" refers herein to a chemical composition having the chemical structure as shown below, and/or as described in U.S. Pat. No. 8,604,016 and/or U.S. Pat. No. 8,865,718.

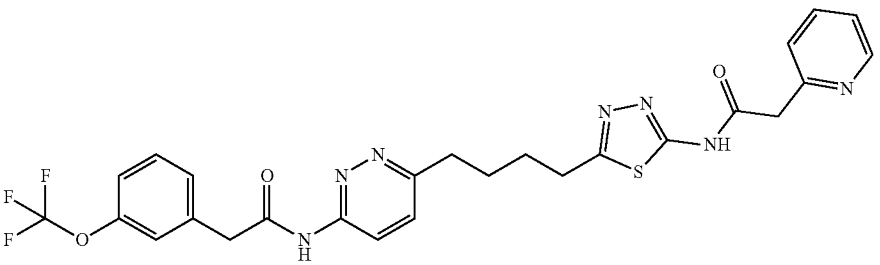 [SMILES: O=C(Cc1cccc(OC(F)(F)F)c1)Nc1ccc(CCCCc2nnc(NC(=O)Cc3ccccn3)s2)nn1]

As disclosed herein, the combination of a YAP1/WWRT1 inhibitor and a Glutaminase inhibitor as additive or synergistic agents is particularly appealing for PH. As such, the identification of the mechanoactivation of glutaminolysis in PH directly sets the stage for applied endeavors to develop novel clinical treatment strategies in this devastating disease. However, since YAP and GLS1 are already known to be ubiquitous and active in controlling cell growth and organ size throughout the body as well as glutamine metabolism, designing an effective chronic therapy for YAP and GLS1 inhibition in PH while minimizing side effects necessitates local rather than systemic delivery. Local lung delivery via inhalation of verteporfin and CB-839 can achieve that goal. To do so, generated herein were therapeutic particles comprises a biocompatible polymer (such as, for example, a poly(lactic-co-glycolytic) acid (PLGA)) drug delivery system for application as an inhaled and controlled-release form of verteporfin and CB-839, singly or in combination, to target the pulmonary vascular compartment (FIG. 1).

In one aspect, disclosed herein are therapeutic particles comprising a biocompatible polymer. Such biocompatible polymers can provide structure for the delivery of the YAP1/WWRT1 inhibitor and/or Glutaminase inhibitor and also can serve to slowly release the YAP1/WWRT1 inhibiting agent and/or the glutaminase inhibiting agent into tissue. As used herein biocompatible polymers include, but are not limited to polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol), polyhydroxyacids such as poly(lactic acid), poly (gly colic acid), and poly (lactic acid-co-glycolic acids); polyhydroxyalkanoates such as poly3-hydroxybutyrate or poly4-hydroxybutyrate; polycaprolactones; poly (orthoesters); polyanhydrides; poly(phosphazenes); poly (lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof. Biocompatible polymers can also include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly (isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly(ortho esters), poly(ethylene amines), poly(caprolactones), poly(hydroxybutyrates), poly(hydroxyvalerates), polyanhydrides, poly(acrylic acids), polyglycolides, poly(urethanes), polycarbonates, polyphosphate esters, polyphospliazenes, derivatives thereof, linear and branched copolymers and block copolymers thereof, and blends thereof. In some embodiments the particle contains biocompatible and/or biodegradable polyesters or polyanhydrides such as poly(glycolic acid), poly(lactic-co-glycolic acid), poly(vinyl alcohol) (PVA), and/or methacrylate PVA(m-PVA). Other examples of diblock copolymers that can be used in the micelles disclosed herein comprise a polymer such as, example, polyethylene glycol (PEG), polyvinyl acetate, polyvinyl alcohol (PVA), polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic) acid, poly(lactic co-glycolic) acid (PLGA), cellulose derivatives, such as hydroxymethylcellulose, hydroxypropylcellulose and the like. The particles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide$_5$ collectively referred to herein as "PLA", and caprolactone units, such as poly(e-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers. Accordingly, disclosed herein are therapeutic particles comprising a biocompatible polymer (such as, for example, a poly(lactic-co-glycolic) acid (PLGA)), a YAP1/WWRT1 inhibiting agent (such as, for example, verteporfin) and a glutaminase inhibiting agent (such as, for example, CB-839 and/or C968).

It is understood and herein contemplated that the porosity (either in size or number of pores) of the biocompatible polymer can affect the release rate of any YAP1/WWRT1 inhibiting agent and/or glutaminase inhibiting agent which are encapsulated in the particle. Accordingly, disclosed herein are therapeutic particles, wherein the polymer used to make the therapeutic particle is porous and therapeutic particles, wherein the polymer used to make the therapeutic particle is nonporous. In some aspects, the YAP1/WWRT1 inhibiting agent and/or glutaminase inhibiting agent can be double encapsulated by different polymers (i.e., a polymer encapsulating the inhibiting agent which in turn is encapsulated by another polymer which could have a different rate of degradation).

It is understood and herein contemplated that the particles may have any desired size for the intended use. For example, the particles may have any diameter from about 10 nm to about 50 μm. The particle can have a diameter from about 100 nm to about 40 μm, from about 500 nm to about 30 μm, from about 1 μm to about 20 μm, from about 10 μm to about 15 μm. For example, the particle can have a diameter of about 10, 20, 30, 40, 50, 60, 70, 80, 90, 100, 200, 300, 400, 500, 600, 700, 800, 900 nm, 1, 2, 3, 4, 5, 6, 7, 8 9, 10, 11, 12, 13, 14, 15, 16, 17, 18, 19, 20, 25, 30, 35, 40, 45, 50 μm.

As noted above, the polymer make-up, porosity, and size of the biocompatible polymers can affect the rate of release of the YAP1/WWRT1 inhibitor and/or glutaminase inhibitor in the particle. In one aspect, it is contemplated that the YAP1/WWRT1 inhibitor and/or glutaminase inhibitor can be released from the particle over a period of 1, 2, 3, 4, 5, 6, 7, 8, 9, 10, 11, 12, 13, 14, 15, 16, 17, 18, 19, 20, 21, 22, 23, 24, 36, 48, 60, 72 hours, 4, 5, 6, 7, 8, 9, 10, 11, 12, 13, 14, 15, 16, 17, 18, 19, 20, 21, 22, 23, 24, 25, 26, 27, 28, 29, 30, 31, 45, 60, 75, 90, 120, 150, or 180 days. In some embodiments, the size of the particles and porosity allows for fast release kinetics, such that verteporfin and glutaminase inhibitors can be released within 1 to 180 days, more specifically, between about 1 and about 30 days, even more specifically between about 1 and about 7 days, most specifically between 1 and 3 days. Lastly, in some embodiments, the size of the particles in conjunction with glutaminase inhibitors can prevent immune mediated clearance of the particles in the lungs.

In one aspect, it is understood and herein contemplated that while the therapeutic particles disclosed herein can comprise both a YAP1/WWRT1 inhibiting agent and a glutaminase inhibiting agent, to be an effective treatment, it is not necessary for the glutaminase inhibiting agent to be administered in the same therapeutic particle with the YAP1/WWRT1 inhibiting agent. Therefore, disclosed herein are therapeutic particles comprising a biocompatible polymer and a YAP1/WWRT1 inhibiting agent, but not a glutaminase inhibiting agent (a first therapeutic agent). Also disclosed herein are therapeutic particles comprising a biocompatible polymer and a glutaminase inhibiting agent, but not a YAP1/WWRT1 inhibiting agent (a second therapeutic agent). It is understood that when designed to be on separate therapeutic particles, the first and second therapeutic particles can be formulated into the same therapeutic composition for single administration of both the first and second therapeutic particles (i.e., as a single formulation). Thus, in one aspect disclosed herein are pharmaceutical compositions comprising a therapeutic particle comprising a biocompatible polymer, a YAP1/WWRT1 inhibiting agent, and a glutaminase inhibiting agent. Alternatively, disclosed herein are pharmaceutical compositions comprising a first therapeutic particle comprising a biocompatible polymer and a YAP1/WWRT1 inhibiting agent and a second therapeutic particle comprising a biocompatible polymer and a glutaminase inhibiting agent. Also disclosed are pharmaceutic compositions comprising a therapeutic particle comprising a biocompatible polymer and a YAP1/WWRT1 inhibiting agent or a glutaminase inhibiting agent.

The therapeutic particles disclosed herein can be used in the treatment, reduction, inhibition, and/or prevention of pulmonary disease. In one aspect, disclosed herein are methods of treating, inhibiting, reducing, and/or preventing a pulmonary disease (such as, for example, pulmonary vascular disease, pulmonary hypertension, pulmonary arterial hypertension, pulmonary stiffness, pulmonary fibrosis, chronic obstructive pulmonary disease (COPD), cystic fibrosis, emphysema, asthma, pulmonary embolism, acute lung disease, sepsis, tuberculosis, sarcoidosis, pulmonary inflammation due to microbial infection (such as, for example, pneumonia and influenza), or lung cancer (such as small cell lung cancer and non-small cell lung cancer) in a subject in need of such treatment comprising administering a therapeutically effective amount of any of the therapeutic particle comprising a biocompatible polymer, a YAP1/WWRT1 inhibiting agent, and/or a glutaminase inhibiting agent disclosed herein to the subject.

The terms "treat," "treating," "treatment" and grammatical variations thereof as used herein, include partially or completely delaying, alleviating, mitigating or reducing the intensity of one or more attendant symptoms of a disease and/or alleviating, mitigating or impeding one or more causes of a disease. Treatments according to the invention may be applied preventively, prophylactically, palliatively or remedially. Prophylactic treatments are administered to a subject prior to onset (e.g., before obvious signs of disease), during early onset (e.g., upon initial signs and symptoms of disease), or after an established development of disease. Prophylactic administration can occur for several days to years prior to the manifestation of symptoms of an infection. In some instances, the terms "treat," "treating," "treatment" and grammatical variations thereof, include partially or completely reducing pulmonary hypertension, pulmonary arterial hypertension and/or vascular stiffness as compared with prior to treatment of the subject or as compared with the incidence of such symptom in a general or study population. The reduction can be by 5%, 10%, 20%, 30%, 40% or more.

"Administration" to a subject includes any route of introducing or delivering to a subject the therapeutic particles and any YAP1/WWRT1 inhibiting agent and/or glutaminase inhibiting agent delivered on the particle in conjunction with said particle (including simultaneous, concurrent or sequential administration). Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. For example, locally administered agents are easily detectable in the local vicinity of the point of administration but are undetectable or detectable at negligible amounts in distal parts of the subject's body. Administration includes self-administration and the administration by another.

In one aspect, the disclosed methods of treating/reducing/preventing/inhibiting pulmonary disease in a subject comprising administering to the subject any of the therapeutic particle comprising a biocompatible polymer, a YAP1/WWRT1 inhibiting agent, and/or a glutaminase inhibiting agent disclosed herein can comprise administration of the therapeutic particle at any frequency appropriate for the treatment, reduction, prevention, and/or inhibition of pulmonary disease. For example, the therapeutic particles can be administered to the patient at least once every 12, 14, 16, 18, 20, 22, 24, 26, 28, 30, 32, 34, 36, 38, 40, 42, 44, 46, 48 hours, once every 3, 4, 5, 6, 7, 8, 9, 10, 11, 12, 13, 14, 15, 16, 17, 18, 19, 20, 21, 22, 23, 24, 25, 26, 27, 28, 29, 30, 31 days, once every 2, 3, 4, 5, 6, 7, 8, 9, 10, 11, or 12 months. In one aspect, the particles are administered at least 1, 2, 3, 4, 5, 6, 7 times per week.

It is understood and herein contemplated that the therapeutic particles can be formulated to comprise one of a YAP1/WWRT1 inhibitor or a glutaminase inhibitor or both a YAP1/WWRT1 inhibitor and a glutaminase inhibitor. Where the therapeutic particle comprises either the YAP1/WWRT1 inhibitor or the glutaminase inhibitor, contemplated herein are methods of treating pulmonary disease where a therapeutic particle comprising a biocompatible polymer and a YAP1/WWRT1 inhibiting agent, but not a glutaminase inhibiting agent is formulated in a composition with a second therapeutic particle comprising a biocompatible polymer and a glutaminase inhibiting agent, but not a YAP1/WWRT1 inhibiting agent and administered in a single dose or, alternatively the first and second therapeutic particles are formulated separately and administered concurrently or sequentially. In one aspect, where the first therapeutic particle comprises a biocompatible polymer and a YAP1/WWRT1 inhibiting agent is formulated separately from the second therapeutic particle comprising a biocompatible polymer and a glutaminase inhibiting agent, it is understood and herein contemplated that either the order of the administration of the first and second therapeutic agents does not matter. In one aspect, the second therapeutic agent can be administered at least 1, 2, 3, 4, 5, 6, 7 8, 9, 10, 15, 20, 25, 30, 35, 40, 45, 50, 55 seconds, 1, 2, 3, 4, 5, 6 7, 8, 9 10, 15, 20, 25, 30, 35, 40, 45, 50, 55 minutes, 1, 2, 3, 4, 5, 6, 7 8, 9, 10, 11, 12, 18, 24, 30, 36, 42, 48, 60, 72 hours after the first therapeutic agent (or vice versa if the second therapeutic agent is administered first).

In one aspect, it is understood and herein contemplated that to be an effective treatment, it is not necessary for the glutaminase inhibiting agent to be administered in the same therapeutic particle with the YAP1/WWRT1 inhibiting agent. As noted above, the glutaminase inhibiting agent can be administered either as a lone composition or as part of a second therapeutic particle comprising the glutaminase inhibitor, but not the YAP1/WWRT1 inhibitor. The glutaminase inhibiting agent either in a composition or as a second therapeutic particle can be administered systemically or locally (i.e., to the lungs by any lung directed administration route disclosed herein).

1. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. When used in reference to administration to a human, the term generally implies the component has met the required standards of toxicological and manufacturing testing or that it is included on the Inactive Ingredient Guide prepared by the U.S. Food and Drug Administration.

The term "pharmaceutically acceptable carrier" means a carrier or excipient that is useful in preparing a pharmaceutical composition that is generally safe and non-toxic, and includes a carrier that is acceptable for veterinary and/or human pharmaceutical use or therapeutic use. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below. The term "carrier" includes phosphate buffered saline solution, water, emulsions (such as an oil/water or water/oil emulsion) and/or various types of wetting agents as well as a biocompatible polymer such as poly(lactic-co-glycolic) acid, also referred to herein as PLGA. The pharmaceutical compositions also can include preservatives. A "pharmaceutically acceptable carrier" as used in the specification and claims includes both one and more than one such carrier. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

The terms "pharmaceutically effective amount," "therapeutically effective amount," or "therapeutically effective dose" include that amount of a composition such as a YAP1/WWRT1 inhibiting composition and/or a GLS1 inhibiting composition, that, when administered, is sufficient to prevent development of, or alleviate to some extent, one or more of the symptoms of the disease being treated. The therapeutically effective amount will vary depending on the composition such as a YAP1/WWRT1 inhibiting composition and/or a GLS1 inhibiting composition, the disease and its severity, the route of administration, time of administration, rate of excretion, drug combination, judgment of the treating physician, dosage form, and the age, weight, general health, sex and/or diet of the subject to be treated. In the context of the present method, a pharmaceutically or therapeutically effective amount or dose of a YAP1/WWRT1 inhibiting composition and/or a glutaminase inhibiting composition, includes an amount that is sufficient to treat pulmonary disease, such as pulmonary hypertension, pulmonary arterial hypertension and/or pulmonary vascular stiffness, but also including, but not limited to pulmonary fibrosis, chronic obstructive pulmonary disease (COPD), cystic fibrosis, emphysema, asthma, pulmonary embolism, acute lung disease, sepsis, tuberculosis, sarcoidosis, pulmonary inflammation due to microbial infection (such as, for example, pneumonia and influenza), and lung cancer (such as small cell lung cancer and non-small cell lung cancer).

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The terms "pharmaceutically effective amount," "therapeutically effective amount," or "therapeutically effective dose" refer to the amount of a composition such as an YAP1/WWRT1 inhibiting composition and/or a GLS1 inhibiting composition, that will elicit the biological or medical response of a tissue, system, animal, or human that is being sought by the researcher, veterinarian, medical doctor or other clinician. In some embodiments, a desired response is a treatment of a vascular disease such as pulmonary hypertension, pulmonary arterial hypertension and/or or pulmonary vascular stiffness. Such treatment can be quantified by determining one or more of right ventricular systolic pressure (RVSP), right ventricular hypertrophy (Fulton index, RV/LV+S), vascular remodelling, and arteriolar muscularization.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

C. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Simultaneous Pharmacologic Inhibition of YAP1 and GLS1 Via Inhaled PLGA-Encapsulated Particles Improves Pulmonary Hypertension Pulmonary hypertension (PH) is a poorly understood vascular disease with increasing prevalence worldwide but with inadequate treatment options. There exist over a dozen approved vasodilator drugs for treatment of this disease; nonetheless, mortality with current therapies remains high. At the cellular and molecular levels in the diseased pulmonary vasculature, PH is characterized by metabolic dysregulation, pro-proliferative states, and adverse pulmonary vascular remodeling and stiffness. As such, there have been recent efforts to develop novel pharmacologic approaches that target the molecular origins of PH and thus could represent disease-modifying opportunities. Herein is shown that a key molecular connection between vessel stiffness and metabolic dysregulation that promotes PH. Namely, it was found that vessel stiffness mechanoactivates the YAP1/WWRT1 co-transcription factors to induce glutaminolysis via induction of glutaminase (GLS1), thus sustaining the metabolic needs of proliferating pulmonary vascular cells and driving PH in vivo.

These molecular insights advanced the paradigm of vascular stiffness beyond merely a consequence of long-standing vascular dysfunction but rather as a specific metabolic cause of vascular cell proliferation and PH development. Importantly, it was demonstrated substantial reversal of PH in a monocrotaline rat model of PH by pharmacologic inhibitors of YAP1 (verteporfin) and glutaminase (such as, for example, CB-839 and/or C968). When delivered systemically, these drugs improved the hemodynamic and histopathologic manifestations of PH by decreasing the hyperproliferative phenotypes of diseased vascular cells. Additional findings have been independently reported that emphasize the direct importance of YAP signaling and glutamine metabolism in the pathogenesis of PH. Specifically, the YAP inhibitor verteporfin is an already FDA-approved drug for use in age-related macular degeneration. CB-839 is a glutaminase inhibitor that is in clinical trial for kidney cancer (Clinical Trial NCT02071862). Thus, verteporfin and CB-839 are promising candidates for re-purposing for treatment of PH in humans. Their combination as additive or synergistic agents is particularly appealing for PH. As such, the identification of the mechanoactivation of glutaminolysis in PH directly sets the stage for applied endeavors to develop novel clinical treatment strategies in this devastating disease.

However, since YAP1 and GLS1 are already known to be ubiquitous and active in controlling cell growth and organ size throughout the body as well as glutamine metabolism, designing an effective chronic therapy for YAP1 and GLS1 inhibition in PH while minimizing side effects necessitates local rather than systemic delivery. Local lung delivery via inhalation of verteporfin and CB-839 can achieve that goal. To do so, generated herein was a poly(lactic-co-glycolytic) acid (PLGA) drug delivery system for application as an inhaled and controlled-release form of verteporfin and CB-839, singly or in combination, to target the pulmonary vascular compartment (FIG. 1).

a) Materials and Methods (1) PLGA Microparticle Fabrication

PLGA microparticles were fabricated using a single emulsion-evaporation technique. For all the microparticles, Poly (lactic-co-glycolic) acid (PLGA-50:50 lactide:glycolide, ester terminated) (MW:38,000-54,000) (viscosity: 0.45-0.6 dL/g) (Sigma Aldrich, MO) were utilized. Specifically, 50 mg of PLGA was dissolved in 4 ml of dichloromethane (DCM—Sigma Aldrich, MO). For single drug encapsulation 4 mg of CB-839 or verteporfin were directly dissolved in DCM containing PLGA. In case of combinatorial drug encapsulation, 4 mg each of CB-839 and verteporfin were added to DCM containing PLGA. In case of IR780 microparticles, 5 mg of IR780 was added to the DCm solution containing PLGA. In case of blank particle generation, PLGA dissolved in DC was used as-is. Next, this solution was then added to 60 ml of 2% polyvinyl-alcohol (PVA, MW~25,000, 98% hydrolyzed; PolySciences) and homogenized (L4RT-A, Silverson, procured through Fisher Scientific) at 10,000 rpm for 3 min. The homogenized mixtures were then added to 40 ml of 1% PVA on stir plate and left for 2 hours in order for the DCM to evaporate. After 2 hours, the microparticles were centrifuged (2000 g, 5 min, 4° C.), washed 5 times with deionized water, and lyophilized for 48 hours (Virtis Benchtop K freeze dryer, Gardiner, NY).

(2) Characterization of Microparticles, Assessment of Encapsulation and Release Kinetics.

The morphology of the microparticles was characterized using scanning electron microscopy (SEM—JEOL JSM6510) and the average size of the blank microparticles was determined using dynamic light scattering (Malvern, Worcestershire, UK). The release kinetics of the drugs from PLGA microparticles was determined by incubating 1 mg of microparticles with or without drugs in 1 mL of 0.2% tween 80 (Fisher Scientific, Pittsburgh, PA) in centrifuge tubes on end-over-end rotator at 37° C. Every day for 10 days, the tubes were centrifuged at 2000 g for 5 min, 0.8 mL of the supernatant was retrieved and frozen at −20° C., and 0.8 mL of fresh 0.2% tween 80 was replaced in the tubes. These tubes were then returned to the incubator.

In order to assess the concentration of verteporfin, UV-vis spectroscopy plate reader (SpectraMax, Molecular Devices, Sunnyvale, CA) was utilized. An absorbance spectrum indicated that the maximum peak absorption of verteporfin is at 440 nm. Using this wavelength, a standard curve was plotted, and the concentration of the released verteporfin from microparticles was determined. The cumulative amount of verteporfin released from the microparticles was quantified and utilized to determine the percentage encapsulation efficiency and percentage loading.

In order to assess the concentration of CB-839, a high-performance liquid chromatography (HPLC Ultimate 3000, Fisher Scientific, Pittsburgh, PA) protocol was developed. Specifically, 18C column, 5 μm, 4.6×150 mm were utilized with the mobile phase of 80:20 water:methanol, at 1 mL/min flow rate for 10 min and the absorbance was recorded at 210 nm. A standard curve of CB-839 in 0.2% tween 80 was generated and utilized to quantify the concentration of the drug released over time. The cumulative amount of CB-839 released from the microparticles was utilized to determine the percentage encapsulation efficiency and percentage loading.

(3) Cell Culture.

Primary human pulmonary arterial endothelial cells (PAECs) were grown in EGM-2 cell culture media (Lonza), and experiments were performed at passages 3 to 6.

(4) Animals.

Monocrotaline-treated rats: Male Sprague-Dawley rats (10-14 week old) were injected with 60 mg/kg monocrotaline at time 0; at 0-4 weeks post-exposure, right heart catheterization was performed followed by harvest of lung tissue for RNA extraction or OCT embedding, as described below (section: Tissue harvest). At day 0, 7, 14, intratracheal aerosol administration of saline vs PLGA microparticles (1 mg of microparticles per dose in 0.25 mL of saline) was performed in isoflurane anesthetized rats.

(5) Tissue Harvest of Rat Lungs.

After physiological measurements, by direct right ventricular puncture, the pulmonary vessels were gently flushed with 1 cc of saline to remove the majority of blood cells, prior to harvesting cardiopulmonary tissue. The heart was removed, followed by dissection and weighing of the right ventricle (RV) and of the left ventricle+septum (LV+S). Organs were then harvested for histological preparation or flash frozen in liquid N2 for subsequent homogenization and extraction of RNA and/or protein. To further process lung tissue specifically, prior to excision, lungs were flushed with PBS at constant low pressure (~10 mmHg) via right ventricular cannulation, followed by tracheal inflation of the left lung with OCT (Sigma Aldrich) at a pressure of ~20 cm H2O. Lung tissue was embedded in OCT and frozen on top of liquid $N_2$ for storage at −80° C. before being sliced into 5 μm cryostat sections.

(6) Cryostaining and Confocal Immunofluorescence of Lung Sections.

Cryostat sections were cut from OCT embedded lung tissues at 5-10 μm and mounted on gelatin-coated histological slides. Slides were thawed at room temperature for 10-20 min and rehydrated in wash buffer for 10 min. All sections were blocked in 10% donkey serum and exposed to primary antibody and Alexa 488, 568 and 647-conjugated secondary antibodies (Thermo Fisher Scientific) for immunofluorescence. DAPI was obtained from Sigma-Aldrich. Primary antibody against α-SMA (ab32575; 1/1000 and ab21027; 1/300) were purchased from Abcam. A primary antibody against PCNA (13-3900, 1/100) was purchased from Thermo Fisher Scientific. Pictures were obtained using a Nikon A1 confocal microscope. Small pulmonary vessels (<100 μm diameter) present in a given tissue section (>10 vessels/section) that were not associated with bronchial airways were selected for analysis (N>5 animals/group). Intensity of staining was quantified using ImageJ software (NIH). Vessel thickness was calculated. All measurements were performed blinded to condition.

(7) Picrosirius Red Stain and Quantification.

Picrosirius red stain was achieved through the use of 5 μm sections stained with 0.1% Picrosirius red (Direct Red80, Sigma-Aldrich) and counterstained with Weigert's hematoxylin to reveal fibrillar collagen. The sections were then serially imaged using with an analyzer and polarizer oriented parallel and orthogonal to each other. Microscope conditions (lamp brightness, condenser opening, objective, zoom, exposure time, and gain parameters) were maintained throughout the imaging of all samples. A minimal threshold was set on appropriate control sections for each experiment in which only the light passing through the orthogonally-oriented polarizers representing fibrous structures (i.e., excluding residual light from the black background) was included. The threshold was maintained for all images across all conditions within each experiment. The area of the transferred regions that was covered by the thresholded light was calculated and at least 10 sections/vessel per condition were averaged together (NIH ImageJ software).

(8) Whole Lung Fluorescence Imaging.

A total of 1 mg of PLGA microparticles encapsulating IR780 dye or blank microparticles were intra-tracheally administered to rats under isoflurane anaesthesia. The rats were returned to their cages for 7 days. After 7 days another set of rats were intra-tracheally administered with 1 mg of PLGA microparticles encapsulating IR780 dye. All the rats were sacrificed and lungs were harvested. The fluorescence in the lungs was determined using IVIS 200 (Perkin Elmer) using ICG excitation, and emission filters.

(9) Statistics.

Cell culture experiments were performed at least three times and at least in triplicate for each replicate. The number of animals in each group was calculated to measure at least a 20% difference between the means of experimental and control groups with a power of 80% and standard deviation of 10%. The number of unique patient samples for this study was determined primarily by clinical availability. In situ expression/histologic analyses of rodent tissue, and pulmonary vascular hemodynamics in mice and rats were performed in a blinded fashion. Numerical quantifications for in vitro experiments using cultured cells or in situ quantifications represent mean±standard deviation (SD). Numerical quantifications for physiologic experiments using rodents or human reagents represent mean±standard error of the mean (SEM). Micrographs are representative of experiments in each relevant cohort. Normality of data distribution was determined by Shapiro Wilk testing. Paired samples were compared by a 2-tailed Student's t test for normally distributed data, while Mann-Whitney U non-parametric testing was used for non-normally distributed data. For comparisons among groups, one-way ANOVA and post-hoc Tukey testing was performed. A P-value less than 0.05 was considered significant.

(10) Study Approval.

All animal experiments were approved by the University of Pittsburgh.

b) Results (1) PLGA Microparticles Encapsulate and Release Verteporfin and CB-839 Simultaneously.

In order to develop a controlled-release formulation that can release verteporfin and CB-839 and block YAP1/WWRT1 and GLS1 simultaneously, PLGA-based microparticles were generated. Specifically, oil in water emulsions were utilized, where verteporfin alone, CB-839 alone or verteporfin with CB-839 together were directly dissolved in the oil phase to generate the microparticles. The size of the microparticles was optimized to be in the 1-5 μm range (as observed using scanning electron microscope and dynamic light scattering—FIG. 2A, 2B) for optimal deposition in the lungs. In the combinatorial delivery microparticle, the percentage encapsulation efficiency (%±SD) and loading (mg/mg±SD) of verteporfin were determined to be 46.5±5% and 0.09±0.01 respectively; and percentage encapsulation efficiency and loading of CB-839 were determined to be 22±4% and 0.04±0.007, respectively. For single drug formulation, percentage encapsulation efficiency and loading of CB-839 was observed to be 46.9±5% and 0.09±0.01 respectively, and percentage encapsulation efficiency and loading of verteporfin were determined to be 85±9% and 0.16±0.02 respectively. Moreover, the release kinetics of verteporfin and CB-839 from different formulations indicated that verteporfin was released in a sustained manner for 6 days, and CB-839 was released for 10 days (FIG. 2C, 2D).

(2) PLGA Microparticles Deposit their Drug Payloads in the Lungs of Rats for 7 Days.

To ensure extended efficacy of drug via controlled release, it was determine that drugs deposited from PLGA microparticles are maintained in lung tissue for the duration of treatment. To do so, PLGA microparticles encapsulating IR780, a near infrared sensor, were generated. The microparticles encapsulating IR780 dye or blank microparticles were administered to rats via a single intra-tracheal aerosol administration. These rats were then sacrificed on day 0 or 7 post-particle delivery; and the lung and heart tissues were harvested and imaged for the presence of the dye. Microparticles were observed to deposit their drug payloads in the lungs of rats, and that this single payload was retained in the lungs for 7 days (FIG. 3).

(3) PLGA Microparticles Delivering Verteporfin and CB-839 Ameliorate Multiple Indices of Pulmonary Hypertension in Monocrotaline-Exposed Rats In Vivo.

PLGA microparticles carrying verteporfin and CB-839, singly or in combination, were tested in vivo to determine their ability to prevent PH in a rodent model of disease. Specifically, PH was induced in rats using monocrotaline (MCT) injections at Day 0 and studied in various groups: blank microparticles, microparticles encapsulating verteporfin alone, microparticles encapsulating CB-839 alone, or microparticles encapsulating both verteporfin+CB-839 delivered intra-tracheally to rats weekly for 3 weeks starting at Day 0 (FIG. 4A). At the end of the third week, hemodynamic (right ventricular systolic pressure, RVSP, which is a surrogate of pulmonary arterial pressures as well as RV/LV+S mass ratio or Fulton index which is a measure of right ventricular hypertrophy), histologic (vascular remodeling as quantified by αSMA thickness of small pulmonary arterioles and vascular matrix remodeling as quantified by picrosirius red staining), and molecular markers (PCNA, a proliferation marker) of PH were quantified among the various comparator groups.

In monocrotaline (MCT) PH rats, PLGA-based delivery of both drugs simultaneously led to significant and substantial decreases of RVSP and Fulton index, as compared with blank microparticles (FIG. 4B). Consistent with efficacy of single drugs alone delivered systemically via serial I.P. administration 2 verteporfin alone also promoted significant decreases (FIG. 4C), and CB-839 demonstrated non-significant trends toward similar improvement (FIG. 4D). By confocal in situ staining of lung tissue and quantification of smooth muscle arteriolar (<100 μm diameter) thickness via a-smooth muscle actin (α-SMA) staining (FIG. 5A), histopathologic pulmonary vascular remodeling of monocrotaline PH rats with saline or blank microparticles was reduced most robustly by simultaneous PLGA delivery of both drugs (FIG. 5C). In comparison, verteporfin delivery alone also decreased remodeling but to a lesser degree (FIG. 5C) as compared with the drug combination; CB-839 delivery alone exhibited a slight but non-significant trend toward improvement of remodeling. By in situ staining of pulmonary arterioles for the proliferation marker PCNA, only the verteporfin+CB-839 combination displayed a significant decrease of the elevated vascular PCNA levels in saline or blank particle controls (FIG. 5B); either verteporfin or CB-839 alone displayed a modest but non-significant decrease of vascular PCNA expression. Finally, by in situ picrosirius red staining to quantify the level of pulmonary vascular matrix remodeling, only the verteporfin+CB-839 combination displayed a significant decrease of both pulmonary arteriolar collagen deposition (non-polarized light) and collagen crosslinking (polarized light) as compared with saline or blank particle controls (FIG. 6). Thus, all indices demonstrated significant and substantial improvement with combination drug delivery. For some indices, either verteporfin or CB-839 alone demonstrated improvement. However, only combination of drug delivery, but neither verteporfin or CB-839 alone, displayed significant improvement across all indices of PH.

c) Discussion

These findings reveal PLGA microparticle encapsulation is effective for controlled and sustained pulmonary vascular delivery of verteporfin and CB-839. These data also prove that such PLGA-based pulmonary delivery of this combination of drugs simultaneously is effective in improving PH in vivo, and performs better when considering multiple indices of disease than either PLGA-based drug delivery alone. As such, these results carry broad implications regarding the development of specific, next-generation drug combinations for pulmonary vascular disease and perhaps for pulmonary conditions beyond PH that affect both normal health and disease.

By coupling local delivery with combination drug therapy, this approach addresses key concerns that have emerged regarding the development of novel therapies for PH. While prior drug development in PH has focused on compounds that target three major vasodilatory pathways, a great majority of next generation of drugs being tested in this disease focus on targeting the proliferative and often metabolic cancer-like phenotypes of the diseased pulmonary vascular cells. In fact, the concept of repurposing chemotherapeutic drugs such as receptor tyrosine kinase inhibitors has been touted and continues to be explored. In parallel, a number of metabolic therapies, such as dicholoroacetate and bardoxolone, have been progressing in clinical trial, designed to reverse metabolic dysfunction in PH. Nonetheless, because of the broad-reaching effects of such anti-proliferative and metabolic therapies, there is growing concern that these therapies may carry substantial risk due to unintended off-target or systemic effects. Clinical trial data have supported that notion, demonstrating substantial adverse effects in PH with the RTK inhibitor imatinib despite its hemodynamic and pulmonary vascular benefits. By using PLGA microparticles for local tissue and pulmonary vascular delivery of such next generation therapies in PH can effectively address these issues, not only by limiting the breadth of tissues affected but also by maximizing the local effective concentration of drug to vascular cells and thus allowing for an overall decrease of drug needed for administration.

Another concern in developing novel pharmacologic therapies in PH that is mitigated by the approach addresses the question of potency of a given next generation drug targeting only a single molecule or pathway. Given the extreme networks of complexity and overlap of mechanisms surrounding metabolic reprogramming and the hyperproliferative state in PH, there can be a substantial chance that targeting a single proliferative or metabolic factor may lead to compensatory responses that obviate the beneficial effects of that single drug. Systematic inhibition of multiple targets in the same pathogenic pathway as in the YAP-GLS1 axis holds a much higher likelihood of achieving more substantial potency and disease modification. Indeed, the findings that the combination of verteporfin and CB-839 performs better across multiple indices of PH than either PLGA-based drug delivery alone strengthen that notion. Coupling these robust effects with local delivery also mitigates the chance of systemic toxicity, facilitating this potency specifically in diseased lung and pulmonary vasculature.

Another advent of this work reflects a new direction for development of locally delivered therapies for PH. While current PH therapies involving inhaled prostacyclin tend to reduce systemic side effects on peripheral vasculature, there has been a delay in development of long-acting, controlled release prostacyclin products that can be used effectively as an inhaled therapy. In the work provided herein, a solution involving PLGA-based microparticles was chosen for a number of reasons. Specifically, PLGA microparticles have an excellent U.S. FDA approval track record. Furthermore, the drugs can be encapsulated and released from these microparticles in a sustained manner. The microparticles can be designed to be in different size ranges (1-5 μm in this report), for effective delivery to the lungs and targeting pulmonary arterioles. The release kinetics of the encapsulated drugs can be tailored so that a sustained release of drugs for 3-4 weeks can be achieved. Moreover, these formulations are also amenable to be functionalized with different molecules to prevent macrophage mediated phagocytosis and clearance. Lastly, other encapsulation and delivery strategies such as metal-organic frameworks, which provide high loading capacity (>50% weight/weight of particle) can be utilized for simultaneous delivery of large quantities of verteporfin and CB-839 to the lungs.

Finally, lung delivery of PLGA-encapsulated drugs that simultaneously target YAP and GLS1 can be effective in pulmonary diseases far beyond PH. For instance, in idiopathic pulmonary fibrosis independent of the development of PH, there is evidence of the pathogenic importance of increased YAP1/WWRT1 activity as well as glutaminolysis. To an even greater extent, YAP1/WWRT1 activation has emerged as a leading therapeutic candidate for multiple types of cancer, including lung cancer. Similarly, development and progression of specific types of lung cancer have displayed a striking dependence on glutaminolysis. While the results do not test the direct effects of PLGA delivery of verteporfin and CB-839, PLGA particle imaging indicates that aerosolized intra-tracheal delivery can attain substantial coverage of lung parenchyma as well as pulmonary vasculature (FIG. 3). Thus, the translation and clinical utility of this specific combination drug delivery can have broad possibilities across diverse aspects of pulmonary disease.

In conclusion, pulmonary delivery of aerosolized PLGA microspheres are effective for sustained drug delivery locally to lung tissue. Using this system, delivery of a combination of drugs targeting the YAP-GLS1 circuit robustly improves multiple indices of PH in vivo and performs better in aggregate than either PLGA-based drug delivery alone. These findings establish a much-needed foundation for further development for locally specific, sustained, and combinatorial therapies in PH and perhaps other lung diseases.

D. REFERENCES

Acharya A P, Carstens M R, Lewis J S, Dolgova N, Xia C Q, Clare-Salzler M J and Keselowsky B G. A cell-based microarray to investigate combinatorial effects of microparticle-encapsulated adjuvants on dendritic cell activation. J Mater Chem B. 2016; 4:1672-1685.
Acharya A P, Clare-Salzler M J and Keselowsky B G. A high-throughput microparticle microarray platform for dendritic cell-targeting vaccines. Biomaterials. 2009; 30:4168-77.
Arnold J J. Age-related macular degeneration: anti-vascular endothelial growth factor treatment. BMJ Clin Evid. 2016; 2016.
Bertero T, Cotrill K A, Lu Y, Haeger C M, Dieffenbach P, Annis S, Hale A, Bhat B, Kaimal V, Zhang Y Y, Graham B B, Kumar R, Saggar R, Saggar R, Wallace W D, Ross D J, Black S M, Fratz S, Fineman J R, Vargas S O, Haley K J, Waxman A B, Chau B N, Fredenburgh L E and Chan S Y. Matrix remodeling promotes pulmonary hypertension through feedback mechanoactivation of the YAP/TAZ-miR-130/301 circuit Cell Reports. 2015; 13:1016-1032.
Bertero T, Lu Y, Annis S, Hale A, Bhat B, Saggar R, Saggar R, Wallace W D, Ross D J, Vargas S O, Graham B B, Kumar R, Black S M, Fratz S, Fineman J R, West J D, Haley K J, Waxman A B, Chau B N, Cottrill K A and Chan S Y. Systems-level regulation of microRNA networks by miR-130/301 promotes pulmonary hypertension. J Clin Invest. 2014; 124:3514-28.
Bertero T, Oldham W M, Cottrill K A, Pisano S, Vanderpool R R, Yu Q, Zhao J, Tai Y, Tang Y, Zhang Y Y, Rehman S, Sugahara M, Qi Z, Gorcsan J, 3rd, Vargas S O, Saggar R, Saggar R, Wallace W D, Ross D J, Haley K J, Waxman A B, Parikh V N, De Marco T, Hsue P Y, Morris A, Simon M A, Norris K A, Gaggioli C, Loscalzo J, Fessel J and Chan S Y. Vascular stiffness mechanoactivates YAP/TAZ-dependent glutaminolysis to drive pulmonary hypertension. J Clin Invest. 2016; 126:3313-35.
Chan S Y and Loscalzo J. Pathogenic mechanisms of pulmonary arterial hypertension. J Mol Cell Cardiol. 2008; 44:14-30.
Chan S Y and Rubin L J. Metabolic dysfunction in pulmonary hypertension: From basic science to clinical practice European Respiratory Review: An Official Journal of the European Respiratory Society. 2017; 26:pii: 170094.
Dieffenbach P B, Haeger C M, Coronata A M F, Choi K M, Varelas X, Tschumperlin D J and Fredenburgh L E. Arterial stiffness induces remodeling phenotypes in pulmonary artery smooth muscle cells via YAP/TAZ-mediated repression of cyclooxygenase-2. Am J Physiol Lung Cell Mol Physiol. 2017; 313:L628-L647.
Dumas S J, Bru-Mercier G, Courboulin A, Quatredeniers M, Rucker-Martin C, Antigny F, Nakhleh M K, Ranchoux B, Gouadon E, Vinhas M C, Vocelle M, Raymond N, Dorfmuller P, Fadel E, Perros F, Humbert M and Cohen-Kaminsky S. NMDA-Type Glutamate Receptor Activation Promotes Vascular Remodeling and Pulmonary Arterial Hypertension. Circulation. 2018.
Dupont S, Morsut L, Aragona M, Enzo E, Giulitti S, Cordenonsi M, Zanconato F, Le Digabel J, Forcato M, Bicciato S, Elvassore N and Piccolo S. Role of YAP/TAZ in mechanotransduction. Nature. 2011; 474:179-83.
Fisher J D, Acharya A P and Little S R. Micro and nanoparticle drug delivery systems for preventing allotransplant rejection. Clin Immunol. 2015; 160:24-35.
Ge J, Cui H, Xie N, Banerjee S, Guo S, Dubey S, Barnes S and Liu G. Glutaminolysis Promotes Collagen Translation and Stability via alpha-Ketoglutarate-mediated mTOR Activation and Proline Hydroxylation. Am J Respir Cell Mol Biol. 2018; 58:378-390.
Godinas L, Guignabert C, Seferian A, Perros F, Bergot E, Sibille Y, Humbert M and Montani D. Tyrosine kinase inhibitors in pulmonary arterial hypertension: a double-edge sword? Semin Respir Crit Care Med. 2013; 34:714-24.
Hoeper M M, Barst R J, Bourge R C, Feldman J, Frost A E, Galie N, Gomez-Sanchez M A, Grimminger F, Grunig E, Hassoun P M, Morrell N W, Peacock A J, Satoh T, Simonneau G, Tapson V F, Tones F, Lawrence D, Quinn D A and Ghofrani H A. Imatinib mesylate as add-on therapy for pulmonary arterial hypertension: results of the randomized IMPRES study. Circulation. 2013; 127:1128-38.
Hu J, Xu Q, McTiernan C, Lai Y C, Osei-Hwedieh D and Gladwin M. Novel Targets of Drug Treatment for Pulmonary Hypertension. Am J Cardiovasc Drugs. 2015; 15:225-34.
Humbert M, Sitbon O and Simonneau G. Treatment of pulmonary arterial hypertension. N Engl J Med. 2004; 351:1425-36.
Jain R A. The manufacturing techniques of various drug loaded biodegradable poly(lactide-co-glycolide) (PLGA) devices. Biomaterials. 2000; 21:2475-90.
Kudryashova T V, Goncharov D A, Pena A, Kelly N, Vanderpool R, Baust J, Kobir A, Shufesky W, Mora A L, Morelli A E, Zhao J, Ihida-Stansbury K, Chang B, DeLisser H, Tuder R M, Kawut S M, Sillje H H, Shapiro S, Zhao Y and Goncharova E A. HIPPO-Integrin-linked Kinase Cross-Talk Controls Self-Sustaining Proliferation and Survival in Pulmonary Hypertension. Am J Respir Crit Care Med. 2016; 194:866-877.
Liu F, Lagares D, Choi K M, Stopfer L, Marinkovic A, Vrbanac V, Probst C K, Hiemer S E, Sisson T H, Horowitz J C, Rosas T O, Fredenburgh L E, Feghali-Bostwick C, Varelas X, Tager A M and Tschumperlin D J. Mechanosignaling through YAP and TAZ drives fibroblast activation and fibrosis. Am J Physiol Lung Cell Mol Physiol. 2015; 308:L344-57.
Lo Sardo F, Strano S and Blandino G. YAP and TAZ in Lung Cancer: Oncogenic Role and Clinical Targeting. Cancers (Basel). 2018; 10.
Michelakis E D, Gurtu V, Webster L, Barnes G, Watson G, Howard L, Cupitt J, Paterson I, Thompson R B, Chow K, O'Regan D P, Zhao L, Wharton J, Kiely D G, Kinnaird A, Boukouris A E, White C, Nagendran J, Freed D H, Wort S J, Gibbs JSR and Wilkins M R. Inhibition of pyruvate dehydrogenase kinase improves pulmonary arterial hypertension in genetically susceptible patients. Sci Transl Med. 2017; 9.
Pullamsetti S S, Savai R, Seeger W and Goncharova E A. Translational Advances in the Field of Pulmonary Hypertension. From Cancer Biology to New Pulmonary Arterial Hypertension Therapeutics. Targeting Cell Growth and Proliferation Signaling Hubs. Am J Respir Crit Care Med. 2017; 195:425-437.
Ratay M L, Balmert S C, Acharya A P, Greene A C, Meyyappan T and Little S R. TRI Microspheres prevent key signs of dry eye disease in a murine, inflammatory model. Sci Rep. 2017; 7:17527.

Romero R, Sayin V I, Davidson S M, Bauer M R, Singh S X, LeBoeuf S E, Karakousi T R, Ellis D C, Bhutkar A, Sanchez-Rivera F J, Subbaraj L, Martinez B, Bronson R T, Prigge J R, Schmidt E E, Thomas C J, Goparaju C, Davies A, Dolgalev I, Heguy A, Allaj V, Poirier J T, Moreira A L, Rudin C M, Pass H I, Vander Heiden M G, Jacks T and Papagiannakopoulos T. Keapl loss promotes Kras-driven lung cancer and results in dependence on glutaminolysis. Nat Med. 2017; 23:1362-1368.

Schneider C S, Xu Q, Boylan N J, Chisholm J, Tang B C, Schuster B S, Henning A, Ensign L M, Lee E, Adstamongkonkul P, Simons B W, Wang S S, Gong X, Yu T, Boyle M P, Suk J S and Hanes J. Nanoparticles that do not adhere to mucus provide uniform and long-lasting drug delivery to airways following inhalation. Sci Adv. 2017; 3:e1601556.

Zamanian R T, Levine D J, Bourge R C, De Souza S A, Rosenzweig E B, Alnuaimat H, Burger C, Mathai S C, Leedom N, DeAngelis K, Lim A and De Marco T. An observational study of inhaled-treprostinil respiratory-related safety in patients with pulmonary arterial hypertension. Pulm Circ. 2016; 6:329-37.

E. SEQUENCES

WWRT1 polypeptide Amino Acid Sequence

SEQ ID NO: 1

MNPASAPPPLPPPGQQVIHVTQDLDTDLEALFNSVMNPKPSSWRKKILPE

SFFKEPDSGSHSRQSSTDSSGGHPGPRLAGGAQHVRSHSSPASLQLGTGA

GAAGSPAQQHAHLRQQSYDVTDELPLPPGWEMTFTATGQRYFLNHIEKIT

TWQDPRKAMNQPLNHMNLHPAVSSTPVPQRSMAVSQPNLVMNHQHQQQMA

PSTLSQQNHPTQNPPAGLMSMPNALTTQQQQQQKLRLQRIQMERERIRMR

QEELMRQEAALCRQLPMEAETLAPVQAAVNPPTMTPDMRSITNNSSDPFL

NGGPYHSREQSTDSGLGLGCYSVPTTPEDFLSNVDEMDTGENAGQTPMNI

NPQQTRFPDFLDCLPGTNVDLGTLESEDLIPLFNDVESALNKSEPFLTWL

YAP polypeptide amino acid sequence

SEQ ID NO: 2

MDPGQQPPPQ PAPQGQGQPP SQPPQGQGPP SGPGQPAPAA

TQAAPQAPPA GHQIVHVRGD SETDLEALFN AVMNPKTANV

PQTVPMRLRK LPDSFFKPPE PKSHSRQAST DAGTAGALTP

QHVRAHSSPA SLQLGAVSPG TLTPTGVVSG PAATPTAQHL

RQSSFEIPDD VPLPAGWEMA KTSSGQRYFL NHIDQTTTWQ

DPRKAMLSQM NVTAPTSPPV QQNMMNSASG PLPDGWEQAM

TQDGEIYYIN HKNKTTSWLD PRLDPRFAMN QRISQSAPVK

QPPPLAPQSP QGGVMGGSNS NQQQQMRLQQ LQMEKERLRL

KQQELLRQAM RNINPSTANS PKCQELALRS QLPTLEQDGG

TQNPVSSPGM SQELRTMTTN SSDPFLNSGT YHSRDESTDS

GLSMSSYSVP RTPDDFLNSV DEMDTGDTIN QSTLPSQQNR

FPDYLEAIPG TNVDLGTLEG DGMNIEGEEL MPSLQEALSS

DILNDMESVL AATKLDKESF LTWL

-continued

GLS1 amino acid sequence

SEQ ID NO: 3

MMRLRGSGML RDLLLRSPAG VSATLRRAQP LVTLCRRPRG

GGRPAAGPAA AARLHPWWGG GGWPAEPLAR GLSSSPSEIL

QELGKGSTHP QPGVSPPAAP AAPGPKDGPG ETDAFGNSEG

KELVASGENK IKQGLLPSLE DLLFYTIAEG QEKIPVHKFI

TALKSTGLRT SDPRLKECMD MLRLTLQTTS DGVMLDKDLF

KKCVQSNIVL LTQAFRRKFV IPDFMSFTSH IDELYESAKK

QSGGKVADYI PQLAKFSPDL WGVSVCTVDG QRHSTGDTKV

PFCLQSCVKP LKYAIAVNDL GTEYVHRYVG KEPSGLRFNK

LFLNEDDKPH NPMVNAGAIV VTSLIKQGVN NAEKFDYVMQ

FLNKMAGNEY VGFSNATFQS ERESGDRNFA IGYYLKEKKC

FPEGTDMVGI LDFYFQLCSI EVTCESASVM AATLANGGFC

PITGERVLSP EAVRNTLSLM HSCGMYDFSG QFAFHVGLPA

KSGVAGGILL VVPNVMGMMC WSPPLDKMGN SVKGIHFCHD

LVSLCNFHNY DNLRHFAKKL DPRREGGDQR VKSVINLLFA

AYTGDVSALR RFALSAMDME QRDYDSRTAL HVAAAEGHVE

VVKFLLEACK VNPFPKDRWN NTPMDEALHF GHHDVFKILQ

EYQVQYTPQG DSDNGKENQT VHKNLDGLL

GLS1 polypeptide is the GAC isoform amino acid sequence

SEQ ID NO: 4 mmrlrgsgml rdlllrspag vsatlrraqp lvtlcrrprg ggrpaagpaa aarlhpwwgg ggwpaeplar glssspseil qelgkgsthp qpgvsppaap aapgpkdgpg etdafgnseg kelvasgenk ikqgllpsle dllfytiaeg qekipvhkfi talkstglrt sdprlkecmd mlrltlqtts dgvmldkdlf kkcvqsnivl ltqafrrkfv ipdfmsftsh idelyesakk qsggkvadyi pqlakfspdl wgvsvctvdg qrhstgdtkv pfclqscvkp lkyaiavndl gteyvhryvg kepsglrfnk lflneddkph npmvnagaiv vtslikqgvn naekfdyvmq flnkmagney vgfsnatfqs eresgdrnfa igyylkekkc fpegtdmvgi ldfyfqlcsi evtcesasvm aatlanggfc pitgervlsp eavrntlslm hscgmydfsg qfafhvglpa ksgvaggill vvpnvmgmmc wsppldkmgn svkgihfchd lvslcnfhny dnlrhfakkl dprreggdqr hsfgpldyes lqqelalket vwkkvspesn edisttvvyr meslgeks Super-TDU amino acid sequence

SEQ ID NO: 5

SVDD*HF*AKSLGDTWLQIGGSGNPKTANVPQTVP*M*RLRKLPDS*F*FKPPE, peptide 17 amino acid sequence

SEQ ID NO: 6

PQTVPF(3-Cl)RLRK Nle PASFFKPPE

What is claimed is:

1. A method of treating a pulmonary disease in a subject in need thereof comprising administering to the subject a therapeutically effective amount of a therapeutic particle, wherein the therapeutic particle comprises a biocompatible polymer and a composition comprising a YAP1/WWRT1 inhibiting agent and a glutaminase inhibiting agent, wherein the YAP1/WWRT1 inhibiting agent comprises verteporfin, and the glutaminase inhibiting agent comprises CB-839, a salt, prodrug, or derivative thereof, and wherein the therapeutic particle is inhaled and control-released to target a pulmonary vascular compartment.

2. The method of treating a pulmonary disease of claim 1, wherein the pulmonary disease comprises a pulmonary vascular disease, pulmonary hypertension, pulmonary arterial hypertension, pulmonary stiffness, pulmonary fibrosis, chronic obstructive pulmonary disease (COPD), cystic fibrosis, emphysema, asthma, pulmonary embolism, acute lung disease, sepsis, tuberculosis, sarcoidosis, or lung cancer.

3. The method of claim 2, wherein the pulmonary disease is pulmonary hypertension (PH).

4. The method of claim 2, wherein the pulmonary disease is pulmonary arterial hypertension (PAH).

5. The method of claim 1, wherein the biocompatible polymer comprises poly(lactic-co-glycolic) acid (PLGA).

6. The method of claim 1, wherein the particle is from about 1 to 5 micrometers in size.

7. The method of claim 5, wherein the YAP1/WWRT1 inhibiting agent and the glutaminase inhibiting agent are released from the poly(lactic-co-glycolic) acid about 1 day to about 3 days after administration to the subject.

8. The method of claim 1, wherein the YAP1/WWRT1 inhibiting agent is verteporfin, or a salt, prodrug, or derivative thereof.

* * * * *